United States Patent
Song et al.

(10) Patent No.: US 7,439,079 B2
(45) Date of Patent: Oct. 21, 2008

(54) ASSAY DEVICES HAVING DETECTION CAPABILITIES WITHIN THE HOOK EFFECT REGION

(75) Inventors: Xuedong Song, Roswell, GA (US); Paul Christopher, Rhondda Cynon Taf (GB)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 92 days.

(21) Appl. No.: 11/119,262

(22) Filed: Apr. 29, 2005

(65) Prior Publication Data

US 2006/0246601 A1 Nov. 2, 2006

(51) Int. Cl.
| | |
|---|---|
| *G01N 21/00* | (2006.01) |
| *G01N 15/06* | (2006.01) |
| *G01N 33/53* | (2006.01) |
| *G01N 30/02* | (2006.01) |
| *G01N 21/03* | (2006.01) |
| *G01N 21/75* | (2006.01) |
| *G01N 21/76* | (2006.01) |
| *G01N 33/566* | (2006.01) |
| *G01N 33/543* | (2006.01) |
| *C12Q 1/00* | (2006.01) |
| *C12M 1/34* | (2006.01) |
| *C12M 3/00* | (2006.01) |

(52) U.S. Cl. .......................... 436/518; 422/55; 422/68.1; 435/4; 435/7.1; 435/287.1; 435/287.2; 435/287.7; 435/288.7; 436/501; 436/161; 436/164; 436/165; 436/166; 436/169; 436/172; 436/807

(58) Field of Classification Search ................... 422/55, 422/68.1; 435/4, 7.1, 287.1, 287.2, 287.7, 435/288.7; 436/501, 161, 164, 165, 166, 436/169, 172, 807, 518

See application file for complete search history.

(56) References Cited

U.S. PATENT DOCUMENTS 3,700,623 A 10/1972 Keim (Continued)

FOREIGN PATENT DOCUMENTS

| AU | 759407 B2 | 2/2000 |
| EP | 0462376 B1 | 12/1991 |

OTHER PUBLICATIONS

Barbarakis, M.S; Qaisi, W.G; Daunert, S. and L.G. Bachas, "Observation of 'Hook Effects' in the Inhibition and Dose-Response Curves of Biotin Assays Based on the Interaction of Biotinylated Glucose Oxidase with (Strept)avidin," Anal. Chem. vol. 65 (1993) 457-460.*

(Continued)

*Primary Examiner*—Long V. Le
*Assistant Examiner*—Jacqueline Diramio
(74) *Attorney, Agent, or Firm*—Dority & Manning, P.A.

(57) ABSTRACT

A lateral flow assay device for detecting the presence or quantity of an analyte within a test sample is provided. The device utilizes multiple zones, one of which serves as an indicator of whether or not the analyte in the test sample is within the "hook effect" region. Based on this indication, a technique may be selected for correlating a measured signal intensity to an analyte concentration or range of concentrations. For example, when it is determined that the test sample falls outside the "hook effect" region, the analyte concentration may be determined using one portion of a dose response curve. On the other hand, when it is determined that the test sample falls within the "hook effect" concentration, the analyte concentration may be determined using another portion of the dose response curve. Alternatively, the sample may simply be diluted for re-performing the assay. The present inventor has discovered that such a detection technique may simply, quickly and accurately detect an analyte present at any concentration.

23 Claims, 11 Drawing Sheets

U.S. PATENT DOCUMENTS

| | | | |
|---|---|---|---|
| 3,772,076 A | 11/1973 | Keim | |
| 4,094,647 A | 6/1978 | Deutsch et al. | |
| 4,168,146 A | 9/1979 | Grubb et al. | |
| 4,235,601 A | 11/1980 | Deutsch et al. | |
| 4,366,241 A | 12/1982 | Tom et al. | |
| 4,426,451 A | 1/1984 | Columbus | |
| 4,435,504 A | 3/1984 | Zuk et al. | |
| 4,442,204 A | 4/1984 | Greenquist et al. | |
| 4,537,657 A | 8/1985 | Keim | |
| 4,540,659 A | 9/1985 | Litman et al. | |
| 4,595,661 A | 6/1986 | Cragle et al. | |
| 4,614,723 A | 9/1986 | Schmidt et al. | |
| 4,703,017 A | 10/1987 | Campbell et al. | |
| 4,722,889 A | 2/1988 | Lee et al. | |
| 4,742,011 A | 5/1988 | Blake et al. | |
| 4,743,542 A | 5/1988 | Graham, Jr. et al. | |
| 4,743,560 A | 5/1988 | Campbell et al. | |
| 4,806,312 A | 2/1989 | Greenquist | |
| 4,835,099 A | 5/1989 | Mize et al. | |
| 4,843,000 A | 6/1989 | Litman et al. | |
| 4,849,338 A | 7/1989 | Litman et al. | |
| 4,889,816 A | 12/1989 | Davis et al. | |
| 4,904,583 A | 2/1990 | Mapes et al. | |
| 4,920,045 A | 4/1990 | McFarland et al. | |
| 4,954,435 A | 9/1990 | Krauth | |
| 4,956,302 A | 9/1990 | Gordon et al. | |
| 4,963,498 A | 10/1990 | Hillman et al. | |
| 4,978,625 A | 12/1990 | Wagner et al. | |
| 4,980,298 A | 12/1990 | Blake et al. | |
| 5,073,340 A | 12/1991 | Covington et al. | |
| 5,075,077 A | 12/1991 | Durley, III et al. | |
| 5,075,078 A | 12/1991 | Osikowicz et al. | |
| 5,120,643 A | 6/1992 | Ching et al. | |
| 5,120,662 A | 6/1992 | Chan et al. | |
| 5,145,784 A | 9/1992 | Cox et al. | |
| 5,149,622 A | 9/1992 | Brown et al. | |
| 5,185,127 A | 2/1993 | Vonk | |
| 5,208,143 A | 5/1993 | Henderson et al. | |
| 5,208,535 A | 5/1993 | Nakayama et al. | |
| 5,252,459 A | 10/1993 | Tarcha et al. | |
| 5,268,306 A | 12/1993 | Berger et al. | |
| 5,275,785 A | 1/1994 | May et al. | |
| 5,342,759 A | 8/1994 | Litman et al. | |
| 5,387,503 A | 2/1995 | Selmer et al. | |
| 5,395,754 A | 3/1995 | Lambotte et al. | |
| 5,424,220 A | 6/1995 | Goerlach-Graw et al. | |
| 5,428,690 A | 6/1995 | Bacus et al. | |
| 5,464,741 A | 11/1995 | Hendrix | |
| 5,500,350 A | 3/1996 | Baker et al. | |
| 5,516,635 A | 5/1996 | Ekins et al. | |
| 5,518,883 A | 5/1996 | Soini | |
| 5,573,909 A | 11/1996 | Singer et al. | |
| 5,573,919 A | 11/1996 | Kearns et al. | |
| 5,585,279 A | 12/1996 | Davidson | |
| 5,591,581 A | 1/1997 | Massey et al. | |
| 5,591,645 A | 1/1997 | Rosenstein | |
| 5,602,040 A | 2/1997 | May et al. | |
| 5,610,077 A | 3/1997 | Davis et al. | |
| 5,622,871 A | 4/1997 | May et al. | |
| 5,624,537 A | 4/1997 | Turner et al. | |
| 5,637,509 A | 6/1997 | Hemmilä et al. | |
| 5,656,503 A | 8/1997 | May et al. | |
| 5,670,381 A | 9/1997 | Jou et al. | |
| 5,714,389 A | 2/1998 | Charlton et al. | |
| 5,731,147 A | 3/1998 | Bard et al. | |
| 5,753,517 A | 5/1998 | Brooks et al. | |
| 5,780,308 A | 7/1998 | Ching et al. | |
| 5,788,863 A | 8/1998 | Milunic | |
| 5,798,273 A | 8/1998 | Shuler et al. | |
| 5,830,762 A | 11/1998 | Weindel | |
| 5,856,203 A * | 1/1999 | Robinson et al. | 436/518 |
| 5,922,537 A | 7/1999 | Ewart et al. | |
| 5,945,281 A | 8/1999 | Prabhu | |
| 5,962,339 A | 10/1999 | Midgely | |
| 5,968,839 A | 10/1999 | Blatt et al. | |
| 5,989,924 A | 11/1999 | Root et al. | |
| 5,989,926 A | 11/1999 | Badley et al. | |
| 5,998,221 A | 12/1999 | Malick et al. | |
| 6,004,530 A | 12/1999 | Sagner et al. | |
| 6,027,944 A | 2/2000 | Robinson et al. | |
| 6,030,840 A | 2/2000 | Mullinax et al. | |
| 6,057,165 A | 5/2000 | Mansour | |
| 6,077,669 A | 6/2000 | Little et al. | |
| 6,121,008 A * | 9/2000 | Fitzpatrick et al. | 436/518 |
| 6,130,100 A | 10/2000 | Jobling et al. | |
| 6,133,048 A | 10/2000 | Penfold et al. | |
| 6,156,271 A | 12/2000 | May | |
| 6,183,972 B1 | 2/2001 | Kuo et al. | |
| 6,187,269 B1 | 2/2001 | Lancesseru et al. | |
| 6,194,220 B1 | 2/2001 | Malick et al. | |
| 6,242,268 B1 | 6/2001 | Wieder et al. | |
| 6,261,779 B1 | 7/2001 | Barbera-Buillem et al. | |
| 6,274,324 B1 | 8/2001 | Davis et al. | |
| 6,294,391 B1 | 9/2001 | Badley et al. | |
| 6,352,862 B1 | 3/2002 | Davis et al. | |
| 6,362,011 B1 | 3/2002 | Massey et al. | |
| 6,368,875 B1 | 4/2002 | Geisberg | |
| 6,399,398 B1 | 6/2002 | Cunningham et al. | |
| 6,436,651 B1 | 8/2002 | Everhart et al. | |
| 6,444,423 B1 | 9/2002 | Meade et al. | |
| 6,468,741 B1 | 10/2002 | Massey et al. | |
| 6,509,196 B1 | 1/2003 | Brooks et al. | |
| 6,511,814 B1 | 1/2003 | Carpenter | |
| 6,524,864 B2 | 2/2003 | Fernandez de Castro | |
| 6,582,930 B1 | 6/2003 | Ponomarev et al. | |
| 6,585,939 B1 | 7/2003 | Dapprich | |
| 6,613,583 B1 | 9/2003 | Richter et al. | |
| 6,627,459 B1 | 9/2003 | Tung et al. | |
| 6,653,149 B1 | 11/2003 | Tung et al. | |
| 6,669,908 B2 | 12/2003 | Weyker et al. | |
| RE38,430 E | 2/2004 | Rosenstein | |
| 6,818,456 B2 | 11/2004 | Sidewell et al. | |
| 6,951,631 B1 | 10/2005 | Catt et al. | |
| 7,044,919 B1 | 5/2006 | Catt et al. | |
| 7,052,831 B2 | 5/2006 | Fletcher et al. | |
| 2002/0042149 A1 | 4/2002 | Butlin et al. | |
| 2002/0045273 A1 | 4/2002 | Butlin et al. | |
| 2002/0146754 A1 | 10/2002 | Kitawaki et al. | |
| 2003/0100128 A1 * | 5/2003 | Kenjyou et al. | 436/518 |
| 2003/0119202 A1 | 6/2003 | Kaylor et al. | |
| 2003/0119204 A1 | 6/2003 | Wei et al. | |
| 2003/0124739 A1 | 7/2003 | Song et al. | |
| 2003/0139886 A1 | 7/2003 | Bodzin et al. | |
| 2003/0162236 A1 | 8/2003 | Harris et al. | |
| 2004/0029177 A1 * | 2/2004 | Nadaoka et al. | 435/7.1 |
| 2004/0043502 A1 | 3/2004 | Song et al. | |
| 2004/0043507 A1 | 3/2004 | Song et al. | |
| 2004/0043511 A1 | 3/2004 | Song et al. | |
| 2004/0106190 A1 | 6/2004 | Yang et al. | |
| 2004/0121480 A1 | 6/2004 | Wei et al. | |
| 2004/0151632 A1 | 8/2004 | Badley et al. | |
| 2004/0161859 A1 | 8/2004 | Guo et al. | |
| 2004/0197820 A1 | 10/2004 | Wei et al. | |
| 2004/0235189 A1 | 11/2004 | Lu | |
| 2005/0036148 A1 | 2/2005 | Phelan et al. | |
| 2005/0037510 A1 | 2/2005 | Sharrock et al. | |
| 2005/0048599 A1 | 3/2005 | Goldberg et al. | |
| 2005/0107956 A1 * | 5/2005 | Fukunaga et al. | 702/19 |
| 2005/0109951 A1 | 5/2005 | Fish et al. | |

| | | | |
|---|---|---|---|
| 2005/0112635 | A1 | 5/2005 | Gentle et al. |
| 2005/0112779 | A1 | 5/2005 | Wei et al. |
| 2005/0112780 | A1 | 5/2005 | Song |
| 2006/0003390 | A1* | 1/2006 | Schaffler et al. ............. 435/7.9 |
| 2006/0029924 | A1 | 2/2006 | Brewster et al. |
| 2006/0246522 | A1* | 11/2006 | Bhullar et al. ............. 435/7.92 |

FOREIGN PATENT DOCUMENTS

| | | |
|---|---|---|
| EP | 0833159 A2 | 4/1998 |
| EP | 1255111 A1 | 11/2002 |
| EP | 1491892 A1 | 12/2004 |
| WO | WO 97/09620 A | 3/1997 |
| WO | WO 0023805 A1 | 4/2000 |
| WO | WO 03008971 A2 | 1/2003 |
| WO | WO 03008971 A3 | 1/2003 |
| WO | WO 2004034056 A2 | 4/2004 |
| WO | WO 2004034056 A3 | 4/2004 |

OTHER PUBLICATIONS

Article—*A New Tetradentate β-Diketonate-Europium Chelate That Can Be Covalently Bound to Proteins for Time-Resolved Fluoroimmunoassay*, Jingli Yuan et al., Analytical Chemistry, vol. 70, No. 3, Feb. 1, 1998, pp. 596-601.

Article—*Flow-Based Microimunoassay*, Hayes et al., Analytical Chemistry, vol. 73, No. 24, Dec. 15, 2001, pp. 5896-5902.

Article—*One-step all-in-one dry reagent immunoassays with fluorescent europium chelate label and time-resolved fluorometry*, Timo Lövgren, et al., Clinical Chemistry 42:8, 1996, pp. 1196-1201.

Search Report and Written Opinion for PCT/US2006/002252, Jun. 29, 2006.

International Search Report for Int'l Application No. PCT/US2006/016756.

* cited by examiner

ASSAY DEVICES HAVING DETECTION CAPABILITIES WITHIN THE HOOK EFFECT REGION

BACKGROUND OF THE INVENTION

Various analytical procedures and devices are commonly employed in flow-through assays to determine the presence and/or concentration of analytes that may be present in a test sample. For instance, immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that may be used to determine the presence or concentration of that particular antigen in a biological sample.

There are several well-known immunoassay methods that use immunoreactants labeled with a detectable component so that the analyte may be detected analytically. For example, "sandwich-type" assay formats typically involve mixing the test sample with detection probes conjugated with a specific binding member (e.g., antibody) for the analyte to form complexes between the analyte and the conjugated probes. These complexes are then allowed to contact a receptive material (e.g., antibodies) immobilized within the detection zone. Binding occurs between the analyte/probe conjugate complexes and the immobilized receptive material, thereby localizing "sandwich" complexes that are detectable to indicate the presence of the analyte. This technique may be used to obtain quantitative or semi-quantitative results. Some examples of such sandwich-type assays are described in. by U.S. Pat. No. 4,168,146 to Grubb, et al. and U.S. Pat. No. 4,366,241 to Tom, et al. An alternative technique is the "competitive-type" assay. In a competitive assay, the labeled probe is generally conjugated with a molecule that is identical to, or an analog of, the analyte. Thus, the labeled probe competes with the analyte of interest for the available receptive material. Competitive assays are typically used for detection of analytes such as haptens, each hapten being monovalent and capable of binding only one antibody molecule. Examples of competitive immunoassay devices are described in U.S. Pat. No. 4,235,601 to Deutsch, et al., U.S. Pat. No. 4,442,204 to Liotta, and U.S. Pat. No. 5,208,535 to Buechler, et al.

Despite the benefits achieved from these devices, many conventional lateral flow assays encounter significant inaccuracies when exposed to relatively high analyte concentrations. For example, when the analyte is present at high concentrations, a substantial portion of the analyte in the test sample may be left in excess and therefore not form complexes with the conjugated probes. Thus, upon reaching the detection zone, the uncomplexed analyte competes with the complexed analyte for binding sites. Because the uncomplexed analyte is not labeled with a probe, it cannot be detected. Consequently, if a significant number of the binding sites become occupied by the uncomplexed analyte, the assay may exhibit a "false negative." This problem is commonly referred to as the "hook effect" or "prozone".

Various techniques for reducing the "hook effect" in immunoassays have been proposed. For example, U.S. Pat. No. 6,183,972 to Kuo, et al. describes a strip of a porous material through which a test fluid suspected of containing the analyte can flow by capillarity. The strip has at least two distinct capture regions in which immobilized antibodies specific to a first epitope of the analyte are immobilized. Antibodies specific to a second epitope of the analyte are also employed that bear a detectable label. When present at sufficient concentrations, the analyte partially blocks binding of the immobilized antibody with the first epitope of the analyte. Thus, a sandwich of the immobilized antibody, analyte, and labeled antibody is formed in the capture regions. The emitted signal of the labeled antibody in each of the distinct capture regions thus provides a pattern of signals that is unique to the concentration of analyte. The set of signals is mathematically combined to create a monotonous dose-response curve to factor out the blocking of the binding between the immobilized antibody and the first epitope of the analyte.

A need still exists, however, for an improved technique of determining analyte concentration within the "hook effect" region in an accurate, yet simple and cost-effective manner.

SUMMARY OF THE INVENTION

In accordance with one embodiment of the present invention, a lateral flow assay device is disclosed for detecting the presence or quantity of an analyte within a test sample. The lateral flow assay device comprises a porous membrane in communication with conjugated detection probes. The analyte is capable of forming complexes with the conjugated detection probes. The porous membrane defines a detection zone within which a first receptive material is immobilized, the first receptive material being configured to preferentially bind to the analyte, whether complexed or uncomplexed with the conjugated detection probes. The porous membrane also defines an indicator zone located downstream from the detection zone and within which a second receptive material is immobilized. The second receptive material is configured to preferentially bind to uncomplexed conjugated detection probes. The detection zone and indicator zone are capable of producing measurable signals. The intensity of the measurable indicator signal is comparable to a reference standard to determine whether the concentration of the analyte within the test sample is within the hook effect region. The reference standard represents an intensity or range of intensities of the indicator signal at or near a saturation concentration of the analyte.

A method for quantitatively or semi-quantitatively detecting an analyte within a test sample is disclosed. The method comprises contacting the test sample with a porous membrane of a lateral flow device. The porous membrane is in communication with conjugated detection probes and further defines a detection zone and an indicator zone located downstream from the detection zone. The method comprises measuring the intensity of a detection signal produced at the detection zone and the intensity of an indicator signal produced at the indicator zone. The method further comprises comparing the measured indicator signal intensity to a reference standard, the reference standard representing an intensity or range of intensities of the indicator signal at or near a known saturation concentration of the analyte.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
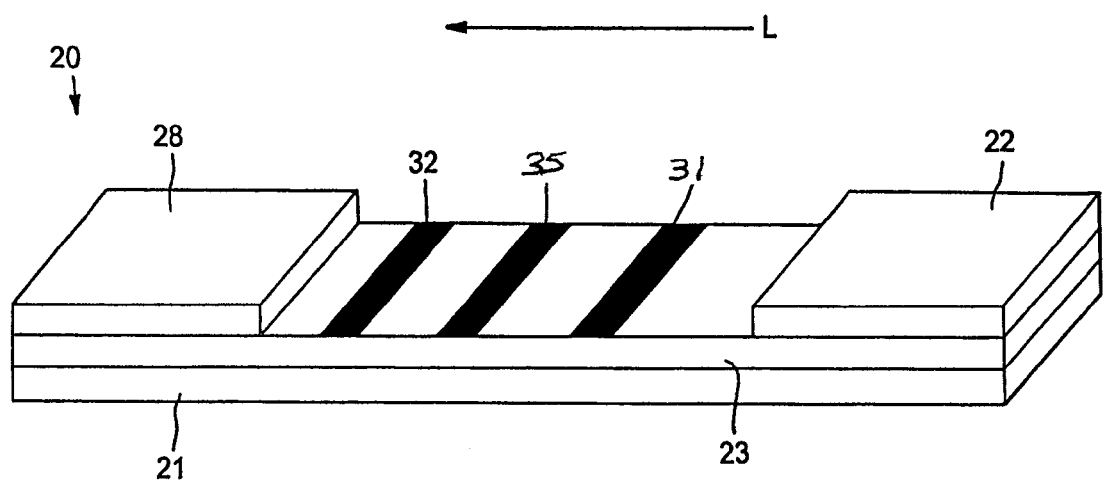
FIG. 1 is a perspective view of one embodiment of a lateral flow assay device of the present invention.

Repeat use of reference characters in the present specification and drawings is intended to represent same or analogous features or elements of the invention.

DETAILED DESCRIPTION OF REPRESENTATIVE EMBODIMENTS

DEFINITIONS

As used herein, the term "analyte" generally refers to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MB (CK-MB); digoxin; phenytoin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 microglobulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. No. 6,436,651 to Everhart, et al. and U.S. Pat. No. 4,366,241 to Tom et al.

As used herein, the term "test sample" generally refers to a biological material suspected of containing the analyte. The test sample may be derived from any biological source, such as a physiological fluid, including, blood, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and so forth. Besides physiological fluids, other liquid samples may be used such as water, food products, and so forth, for the performance of environmental or food production assays. In addition, a solid material suspected of containing the analyte may be used as the test sample. The test sample may be used directly as obtained from the biological source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the analyte.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

In general, the present invention is directed to a lateral flow assay device for detecting the presence or quantity of an analyte within a test sample. The device utilizes multiple zones, one of which serves as an indicator of whether or not the analyte in the test sample is within the "hook effect" region. Based on this indication, a technique may be selected for correlating a measured signal intensity to an analyte concentration or range of concentrations. For example, when it is determined that the test sample falls outside the "hook effect" region, the analyte concentration may be determined using one portion of a dose response curve. On the other hand, when it is determined that the test sample falls within the "hook effect" concentration, the analyte concentration may be determined using another portion of the dose response curve. Alternatively, the sample may simply be diluted for re-performing the assay. The present inventors have discovered that such a detection technique may simply, quickly, and accurately detect an analyte present at any concentration.

Referring to FIG. 1, for instance, one embodiment of a lateral flow assay device 20 that may be formed according to the present invention will now be described in more detail. As shown, the device 20 contains a porous membrane 23 optionally supported by a rigid support material 21. In general, the porous membrane 23 may be made from any of a variety of materials through which the test sample is capable of passing. For example, the materials used to form the porous membrane 23 may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the porous membrane 23 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The size and shape of the porous membrane 23 may generally vary as is readily recognized by those skilled in the art. For instance, a porous membrane strip may have a length of from about 10 to about 100 millimeters, in some embodiments from about 20 to about 80 millimeters, and in some embodiments, from about 40 to about 60 millimeters. The width of the membrane strip may also range from about 0.5 to about 20 millimeters, in some embodiments from about 1 to about 15 millimeters, and in some embodiments, from about 2 to about 10 millimeters. Likewise, the thickness of the membrane strip is generally small enough to allow transmission-based detection. For example, the membrane strip may have a thickness less than about 500 micrometers, in some embodiments less than about 250 micrometers, and in some embodiments, less than about 150 micrometers.

As stated above, the support 21 carries the porous membrane 23. For example, the support 21 may be positioned directly adjacent to the porous membrane 23 as shown in FIG. 1, or one or more intervening layers may be positioned between the porous membrane 23 and the support 21. Regardless, the support 21 may generally be formed from any material able to carry the porous membrane 23. The support 21 may be formed from a material that is transmissive to light, such as transparent or optically diffuse (e.g., transluscent) materials. Also, it is generally desired that the support 21 is liquid-impermeable so that fluid flowing through the membrane 23 does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for the porous membrane 23, the support 21 is generally selected to have a certain minimum thickness. Likewise, the thickness of the support 21 is typically not so large as to adversely affect its optical properties. Thus, for example, the support 21 may have a thickness that ranges from about 100 to about 5,000 micrometers, in some embodiments from about 150 to about 2,000 micrometers, and in some embodiments, from about 250 to about 1,000 micrometers. For instance, one suitable membrane strip having a thickness of about 125 micrometers may be obtained from Millipore Corp. of Bedford, Mass. under the name "SHF180UB25."

As is well known in the art, the porous membrane 23 may be cast onto the support 21, wherein the resulting laminate may be die-cut to the desired size and shape. Alternatively, the porous membrane 23 may simply be laminated to the support 21 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate assay device structures are described in U.S. Pat. No. 5,075,077 to Durley, Ill., et al., which is incorporated herein in its entirety by reference thereto for all purposes.

The device 20 may also contain an absorbent pad 28. The absorbent pad 28 generally receives fluid that has migrated through the entire porous membrane 23. As is well known in the art, the absorbent pad 28 may assist in promoting capillary action and fluid flow through the membrane 23.

To initiate the detection of an analyte within the test sample, a user may directly apply the test sample to a portion of the porous membrane 23 through which it may then travel in the direction illustrated by arrow "L" in FIG. 1. Alternatively, the test sample may first be applied to a sample pad (not shown) that is in fluid communication with the porous membrane 23. Some suitable materials that may be used to form the sample pad include, but are not limited to, nitrocellulose, cellulose, porous polyethylene pads, and glass fiber filter paper. If desired, the sample pad may also contain one or more assay pretreatment reagents, either diffusively or non-diffusively attached thereto.

In the illustrated embodiment, the test sample travels from the sample pad (not shown) to a conjugate pad 22 that is placed in communication with one end of the sample pad. The conjugate pad 22 is formed from a material through which the test sample is capable of passing. For example, in one embodiment, the conjugate pad 22 is formed from glass fibers. Although only one conjugate pad 22 is shown, it should be understood that multiple conjugate pads may also be used in the present invention.

To facilitate accurate detection of the presence or absence of an analyte within the test sample, a predetermined amount of detection probes are applied at various locations of the device 20. Any substance generally capable of producing a signal that is detectable visually or by an instrumental device may be used as detection probes. Suitable detectable substances may include, for instance, luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. No. 5,670,381 to Jou, et al. and U.S. Pat. No. 5,252,459 to Tarcha, et al., which are incorporated herein in their entirety by reference thereto for all purposes. If the detectable substance is colored, the ideal electromagnetic radiation is light of a complementary wavelength. For instance, blue detection probes strongly absorb red light.

In some embodiments, the detectable substance may be a luminescent compound that produces an optically detectable signal. For example, suitable fluorescent molecules may include, but are not limited to, fluorescein, europium chelates, phycobiliprotein, rhodamine, and their derivatives and analogs. Other suitable fluorescent compounds are semiconductor nanocrystals commonly referred to as "quantum dots." For example, such nanocrystals may contain a core of the formula CdX, wherein X is Se, Te, S, and so forth. The nanocrystals may also be passivated with an overlying shell of the formula YZ, wherein Y is Cd or Zn, and Z is S or Se. Other examples of suitable semiconductor nanocrystals may also be described in U.S. Pat. No. 6,261,779 to Barbera-Guillem, et al. and U.S. Pat. No. 6,585,939 to Dapprich, which are incorporated herein in their entirety by reference thereto for all purposes.

Further, suitable phosphorescent compounds may include metal complexes of one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium. The metal complex may contain one or more ligands that facilitate the solubility of the complex in an aqueous or nonaqueous environment. For example, some suitable examples of ligands include, but are not limited to, pyridine; pyrazine; isonicotinamide; imidazole; bipyridine; terpyridine; phenanthroline; dipyridophenazine; porphyrin, porphine, and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

Porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and III, palladium (II) coproporphyrin, ruthenium coproporphyrin, zinc(II)-coproporphyrin-I, derivatives thereof, and so forth. Similarly, some suitable porphine complexes that are capable of exhibiting phosphorescent properties include, but not limited to, platinum(II) tetra-meso-fluorophenylporphine and palladium(II) tetra-meso-fluorophenylporphine. Still other suitable porphyrin and/or porphine complexes are described in U.S. Pat. No. 4,614,723 to Schmidt, et al.; U.S. Pat. No. 5,464,741 to Hendrix; U.S. Pat. No. 5,518,883 to Soini; U.S. Pat. No. 5,922,537 to Ewart, et al.; U.S. Pat. No. 6,004,530 to Sagner, et al.; and U.S. Pat. No. 6,582,930 to Ponomarev, et al., which are incorporated herein in their entirety by reference thereto for all purposes.

Bipyridine metal complexes may also be utilized as phosphorescent compounds. Some examples of suitable bipyridine complexes include, but are note limited to, bis[(4,4'-carbomethoxy)-2,2'-bipyridine]2-[3-(4-methyl-2,2'-bipyridine-4-yl)propyl]-1,3-dioxolane ruthenium(II); bis(2,2'-bipyridine)[4-(butan-1-al)-4'-methyl-2,2'-bi-pyridine] ruthenium(II); bis(2,2'-bipyridine)[4-(4'-methyl-2,2'-bipyridine-4'-yl)-butyric acid]ruthenium(II); tris(2,2'-bipyridine)ruthenium(II); (2,2'-bipyridine)[bis-bis(1,2-diphenylphosphino)ethylene]2-[3-(4-methyl-2,2'-bipyridine-4'-yl)propyl]-1,3-dioxolane osmium(II); bis(2,2'-bipyridine)[4-(4'-methyl-2,2'-bipyridine)-butylamine] ruthenium(II); bis(2,2'-bipyridine)[1-bromo-4(4'-methyl-2,2'-bipyridine-4-yl)butane]ruthenium(II); bis(2,2'-bipyridine) maleimidohexanoic acid, 4-methyl-2,2'-bipyridine-4'-butylamide ruthenium(II), and so forth. Still other suitable metal complexes that may exhibit phosphorescent properties may be described in U.S. Pat. No. 6,613,583 to Richter, et al.; U.S. Pat. No. 6,468,741 to Massey, et al.; U.S. Pat. No. 6,444,423 to Meade, et al.; U.S. Pat. No. 6,362,011 to Massey, et al.; U.S. Pat. No. 5,731,147 to Bard, et al.; and U.S. Pat. No. 5,591,581 to Massey, et al., which are incorporated herein in their entirety by reference thereto for all purposes.

In some cases, luminescent compounds may have a relatively long emission lifetime may have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of a luminescent compound to remain far apart from its emission wavelengths and is desirable because a large difference between excitation and emission wavelengths makes it easier to eliminate the reflected excitation radiation from the emitted signal. Further, a large Stokes shift also minimizes interference from luminescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the luminescent compounds have a Stokes shift of greater than about 50 nanometers, in some embodiments greater than about 100 nanometers, and in some embodiments, from about 100 to about 350 nanometers.

For example, exemplary fluorescent compounds having a large Stokes shift include lanthanide chelates of samarium (Sm (III)), dysprosium (Dy (III)), europium (Eu (III)), and terbium (Tb (III)). Such chelates may exhibit strongly redshifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy may be transferred from the excited chromophore to the lanthanide. This is followed by a fluorescence emission characteristic of the lanthanide. Europium chelates, for instance, have Stokes shifts of about 250 to about 350 nanometers, as compared to only about 28 nanometers for fluorescein. Also, the fluorescence of europium chelates is longlived, with lifetimes of about 100 to about 1000 microseconds, as compared to about 1 to about 100 nanoseconds for other fluorescent labels. In addition, these chelates have a narrow emission spectra, typically having bandwidths less than about 10 nanometers at about 50% emission. One suitable europium chelate is N-(p-isothiocyanatobenzyl)-diethylene triamine tetraacetic acid-$Eu^{+3}$.

In addition, lanthanide chelates that are inert, stable, and intrinsically fluorescent in aqueous solutions or suspensions may also be used in the present invention to negate the need for micelle-forming reagents, which are often used to protect chelates having limited solubility and quenching problems in aqueous solutions or suspensions. One example of such a chelate is 4-[2-(4-isothiocyanatophenyl)ethynyl]-2,6-bis([N, N-bis(carboxymethyl)amino]methyl)-pyridine [Ref: Lovgren, T., et al.; Clin. Chem. 42, 1196-1201 (1996)]. Several lanthanide chelates also show exceptionally high signal-to-noise ratios. For example, one such chelate is a tetradentate β-diketonate-europium chelate [Ref: Yuan, J. and Matsumoto, K.; Anal. Chem. 70, 596-601 (1998)]. In addition to the fluorescent labels described above, other labels that are suitable for use in the present invention may be described in U.S. Pat. No. 6,030,840 to Mullinax, et al.; U.S. Pat. No. 5,585,279 to Davidson; U.S. Pat. No. 5,573,909 to Singer, et al.; U.S. Pat. No. 6,242,268 to Wieder, et al.; and U.S. Pat. No. 5,637,509 to Hemmila, et al., which are incorporated herein in their entirety by reference thereto for all purposes.

Detectable substances, such as described above, may be used alone or in conjunction with a particle (sometimes referred to as "beads" or "microbeads"). For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles that are labeled with a fluorescent or colored dye are utilized. Although any synthetic particle may be used in the present invention, the particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. No. 5,670,381 to Jou, et al.; U.S. Pat. No. 5,252,459 to Tarcha, et al.; and U.S. Patent Publication No. 2003/0139886 to Bodzin, et al., which are incorporated herein in their entirety by reference thereto for all purposes. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc. Metallic particles (e.g., gold particles) may also be utilized in the present invention.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 100 microns, in some embodiments, from about 1 nanometer to about 10 microns, and in some embodiments, from about 10 to about 100 nanometers.

In some instances, it may be desired to modify the detection probes in some manner so that they are more readily able to bind to the analyte. In such instances, the detection probes may be modified with certain specific binding members that are adhered thereto to form conjugated probes. Specific binding members generally refer to a member of a specific binding pair, i.e., two different molecules where one of the molecules chemically and/or physically binds to the second molecule. For instance, immunoreactive specific binding members may include antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin (or derivatives thereof), biotin and streptavidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte (i.e., "analog") may be used so long as it has at least one epitope in common with the analyte.

The specific binding members may generally be attached to the detection probes using any of a variety of well-known techniques. For instance, covalent attachment of the specific binding members to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer because the surface of the detection probe may contain a relatively high surface concentration of polar groups. In addition, although detection probes are often functionalized after synthesis, such as with poly(thiophenol), the detection probes may be capable of direct covalent linking with a protein without the need for further modification. For example, in one embodiment, the first step of conjugation is activation of carboxylic groups on the probe surface using carbodiimide. In the second step, the activated carboxylic acid groups are reacted with an amino group of an antibody to form an amide bond. The activation and/or antibody coupling may occur in a buffer, such as phosphate-buffered saline (PBS) (e.g., pH of 7.2) or 2-(N-morpholino) ethane sulfonic acid (MES) (e.g., pH of 5.3). The resulting detection probes may then be contacted with ethanolamine, for instance, to block any remaining activated sites. Overall, this process forms a conjugated detection probe, where the antibody is covalently attached to the probe. Besides covalent bonding, other attachment techniques, such as physical adsorption, may also be utilized in the present invention.

Referring again to FIG. 1, the porous membrane 23 defines various zones configured to perform the assay. For instance, the porous membrane 23 defines a detection zone 31 that contains a first receptive material. The first receptive material is immobilized on the porous membrane 23 and may be selected from the same materials as the specific binding members described above, including, for instance, antigens; haptens; antibody-binding proteins, such as protein A, protein G, or protein A/G; neutravidin (a deglycosylated avidin derivative), avidin (a highly cationic 66,000-dalton glycoprotein), streptavidin (a nonglycosylated 52,800-dalton protein), or captavidin (a nitrated avidin derivative); primary or secondary antibodies, and derivatives or fragments thereof. In one embodiment, for example, the first receptive material is an antibody specific to an antigen within the test sample. The first receptive material serves as a stationary binding site for complexes formed between the analyte and the conjugated detection probes. Specifically, analytes, such as antibodies, antigens, etc., typically have two or more binding sites (e.g., epitopes). Upon reaching the detection zone 31, one of these binding sites is occupied by the specific binding member of the conjugated probe. However, the free binding site of the analyte may bind to the immobilized first receptive material. Upon being bound to the immobilized receptive material, the complexed probes form a new ternary sandwich complex.

The assay device 20 also contains an indicator zone 35 that is positioned downstream from the detection zone 31. The indicator zone 35 contains a second receptive material that is immobilized on the porous membrane 23. The second receptive material serves as a stationary binding site for the conjugated detection probes. To accomplish the desired binding within the indicator zone 35, it is generally desired that the second receptive material is capable of differentiating between those detection probes that are complexed with the analyte and those that remain uncomplexed. For example, in one embodiment, the second receptive material includes a molecule that has at least one epitope in common with the analyte, such as analyte molecules, or derivatives or fragments (i.e., analog) thereof, so that it is capable of specifically binding to an antibody conjugate when it is uncomplexed with the analyte.

Alternatively, the second receptive material may include a biological material that is not an analyte molecule or analog thereof, but nevertheless is capable of preferentially binding to uncomplexed conjugated detection probes. In one embodiment, for example, the first receptive material may be a monoclonal antibody, such as anti-CRP $IgG_1$. The detection probes are conjugated with a monoclonal antibody different than the monoclonal antibody of the first receptive material, such as anti-CRP $IgG_2$. In this particular embodiment, the second receptive material may be a secondary antibody, such as Goat anti-human, IgG F(ab')$_2$, which has been adsorbed against $F_c$ fragments and therefore reacts only with the $F_{ab}$ portion of IgG. Thus, when no analyte is present, the secondary antibody is able to bind to the free "$F_{ab}$" binding domain of the anti-CRP $IgG_2$ monoclonal antibody. However, when an antigen is present in the test sample, it first complexes with the "$F_{ab}$" binding domain of the anti-CRP $IgG_2$ monoclonal antibody. The presence of the antigen renders the "$F_{ab}$" binding domain unavailable for subsequent binding with the secondary antibody. In this manner, the secondary antibody within the indicator zone 35 is capable of preferentially binding to uncomplexed detection probes.

Although the detection zone 31 and indicator zone 35 provide accurate results, it is sometimes difficult to determine the relative concentration of the analyte within the test sample under actual test conditions. Thus, the assay device 20 may also include a calibration zone 32. In this embodiment, the calibration zone 32 is formed on the porous membrane 23 and is positioned downstream from the detection zone 31 and indicator zone 35. Alternatively, however, the calibration zone 32 may also be positioned upstream from the detection zone 31 and/or indicator zone 35.

The calibration zone 32 is provided with a third receptive material that is capable of binding to any calibration probes that pass through the length of the membrane 23. When utilized, the calibration probes may contain a detectable substance that is the same or different than the detectable substance used for the detection probes. Moreover, the calibration probes may also be conjugated with a specific binding member, such as described above. For example, in one embodiment, biotinylated calibration probes may be used. Generally speaking, the calibration probes are selected in such a manner that they do not bind to the first or second receptive material at the detection zone 31 and indicator zone 35. The third receptive material of the calibration zone 32 may be the same or different than the receptive materials used in the detection zone 31 or indicator zone 35. For example, in one embodiment, the third receptive material is a biological receptive material, such as antigens, haptens, antibody-binding proteins (e.g., protein A, protein G, or protein A/G), neutravidin, avidin, streptavidin, captavidin, primary or secondary antibodies, or complexes thereof. It may also be desired to utilize various non-biological materials for the third receptive material (e.g., polyelectrolytes) of the calibration zone 32, such as described in U.S. Patent Application Publication No. 2003/0124739 to Song, et al., which is incorporated herein in its entirety by reference thereto for all purposes.

When utilized, the polyelectrolytes may have a net positive or negative charge, as well as a net charge that is generally neutral. For instance, some suitable examples of polyelectrolytes having a net positive charge include, but are not limited to, polylysine (commercially available from Sigma-Aldrich Chemical Co., Inc. of St. Louis, Mo.), polyethyleneimine; epichlorohydrin-functionalized polyamines and/or polyamidoamines, such as poly(dimethylamine-co-epichlorohydrin); polydiallyldimethyl-ammonium chloride; cationic cellulose derivatives, such as cellulose copolymers or cellulose derivatives grafted with a quaternary ammonium water-soluble monomer; and so forth. In one particular embodiment, CelQuat® SC-230M or H-100 (available from National Starch & Chemical, Inc.), which are cellulosic derivatives containing a quaternary ammonium water-soluble monomer, may be utilized. Moreover, some suitable examples of polyelectrolytes having a net negative charge include, but are not limited to, polyacrylic acids, such as poly(ethylene-co-methacrylic acid, sodium salt), and so forth. It should also be understood that other polyelectrolytes may also be utilized, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridnium iodide) and poly (styryl-b-acrylic acid), both of which are available from Polymer Source, Inc. of Dorval, Canada.

Although any polyelectrolyte may generally be used, the polyelectrolyte selected for a particular application may vary depending on the nature of the detection probes, the calibration probes, the porous membrane, and so forth. In particular, the distributed charge of a polyelectrolyte allows it to bind to substances having an opposite charge. Thus, for example, polyelectrolytes having a net positive charge are often better equipped to bind with probes that are negatively charged, while polyelectrolytes that have a net negative charge are often better equipped to bind to probes that are positively charged. Thus, in such instances, the ionic interaction between these molecules allows the required binding to occur within the calibration zone 32. Nevertheless, although ionic interaction is primarily utilized to achieve the desired binding in the calibration zone 32, polyelectrolytes may also bind with probes having a similar charge.

Because the polyelectrolyte is designed to bind to probes, it is typically desired that the polyelectrolyte be substantially non-diffusively immobilized on the surface of the porous membrane 23. Otherwise, the probes would not be readily detectable by a user. Thus, the polyelectrolytes may be applied to the porous membrane 23 in such a manner that they do not substantially diffuse into the matrix of the porous membrane 23. In particular, the polyelectrolytes typically form an ionic and/or covalent bond with functional groups present on the surface of the porous membrane 23 so that they remain immobilized thereon. Although not required, the formation of covalent bonds between the polyelectrolyte and the porous membrane 23 may be desired to more permanently immobilize the polyelectrolyte thereon. For example, in one embodiment, the monomers used to form the polyelectrolyte are first formed into a solution and then applied directly to the porous membrane 23. Various solvents (e.g., organic solvents, water, etc.) may be utilized to form the solution. Once applied, the polymerization of the monomers is initiated using heat, electron beam radiation, free radical polymerization, and so forth. In some instances, as the monomers polymerize, they form covalent bonds with certain functional groups of the porous membrane 23, thereby immobilizing the resulting polyelectrolyte thereon. For example, in one embodiment, an ethyleneimine monomer may form a covalent bond with a carboxyl group present on the surface of some porous membranes (e.g., nitrocellulose).

In another embodiment, the polyelectrolyte may be formed prior to application to the porous membrane 23. If desired, the polyelectrolyte may first be formed into a solution using organic solvents, water, and so forth. Thereafter, the polyelectrolytic solution is applied directly to the porous membrane 23 and then dried. Upon drying, the polyelectrolyte may form an ionic bond with certain functional groups present on the surface of the porous membrane 23 that have a charge opposite to the polyelectrolyte. For example, in one embodiment, positively-charged polyethyleneimine may form an ionic bond with negatively-charged carboxyl groups present on the surface of some porous membranes (e.g., nitrocellulose).

In addition, the polyelectrolyte may also be crosslinked to the porous membrane 23 using various well-known techniques. For example, in some embodiments, epichlorohydrin-functionalized polyamines and/or polyamidoamines may be used as a crosslinkable, positively-charged polyelectrolyte. Examples of these materials are described in U.S. Pat. No. 3,700,623 to Keim and U.S. Pat. No. 3,772,076 to Keim, U.S. Pat. No. 4,537,657 to Keim, which are incorporated herein in their entirety by reference thereto for all purposes and are believed to be sold by Hercules, Inc., Wilmington, Del. under the Kymene™ trade designation. For instance, Kymene™ 450 and 2064 are epichlorohydrin-functionalized polyamine and/or polyamidoamine compounds that contain epoxide rings and quaternary ammonium groups that may form covalent bonds with carboxyl groups present on certain types of porous membranes (e.g., nitrocellulose) and crosslink with the polymer backbone of the porous membrane when cured. In some embodiments, the crosslinking temperature may range from about 50° C. to about 120° C. and the crosslinking time may range from about 10 to about 600 seconds.

Although various techniques for non-diffusively immobilizing polyelectrolytes on the porous membrane 23 have been described above, it should be understood that any other technique for non-diffusively immobilizing polyelectrolytic compounds may be used in the present invention. In fact, the aforementioned methods are only intended to be exemplary of the techniques that may be used in the present invention. For example, in some embodiments, certain components may be added to the polyelectrolyte solution that may substantially inhibit the diffusion of such polyelectrolytes into the matrix of the porous membrane 23.

The detection zone 31, indicator zone 35, and calibration zone 32 may each provide any number of distinct detection regions so that a user may better determine the concentration of one or more analytes within a test sample. Each region may contain the same receptive materials, or may contain different receptive materials. For example, the zones may include two or more distinct regions (e.g., lines, dots, etc.). The regions may be disposed in the form of lines in a direction that is substantially perpendicular to the flow of the test sample through the assay device 20. Likewise, in some embodiments, the regions may be disposed in the form of lines in a direction that is substantially parallel to the flow of the test sample through the assay device 20.

In some cases, the membrane 23 may also define a control zone (not shown) that gives a signal to the user that the assay is performing properly. For instance, the control zone (not shown) may contain an immobilized receptive material that is generally capable of forming a chemical and/or physical bond with probes or with the receptive material immobilized on the probes. Some examples of such receptive materials include, but are not limited to, antigens, haptens, antibodies, protein A or G, avidin, streptavidin, secondary antibodies, and complexes thereof. In addition, it may also be desired to utilize various non-biological materials for the control zone receptive material. For instance, in some embodiments, the control zone receptive material may also include a polyelectrolyte, such as described above, that may bind to uncaptured probes. Because the receptive material at the control zone is only specific for probes, a signal forms regardless of whether the analyte is present. The control zone may be positioned at any location along the membrane 23, but is preferably positioned downstream from the detection zone 31 and the indicator zone 35.

Although various embodiments of device configurations have been described above, it should be understood, that a device of the present invention may generally have any configuration desired, and need not contain all of the components described above. Various other device configurations, for instance, are described in U.S. Pat. No. 5,395,754 to Lambotte, et al.; U.S. Pat. No. 5,670,381 to Jou, et al.; and U.S. Pat. No. 6,194,220 to Malick, et al., which are incorporated herein in their entirety by reference thereto for all purposes.

Regardless of their particular configuration of the assay device 20, the indicator zone 35 and detection zone 31 function in tandem to improve the analyte detection accuracy.

Figure 3:
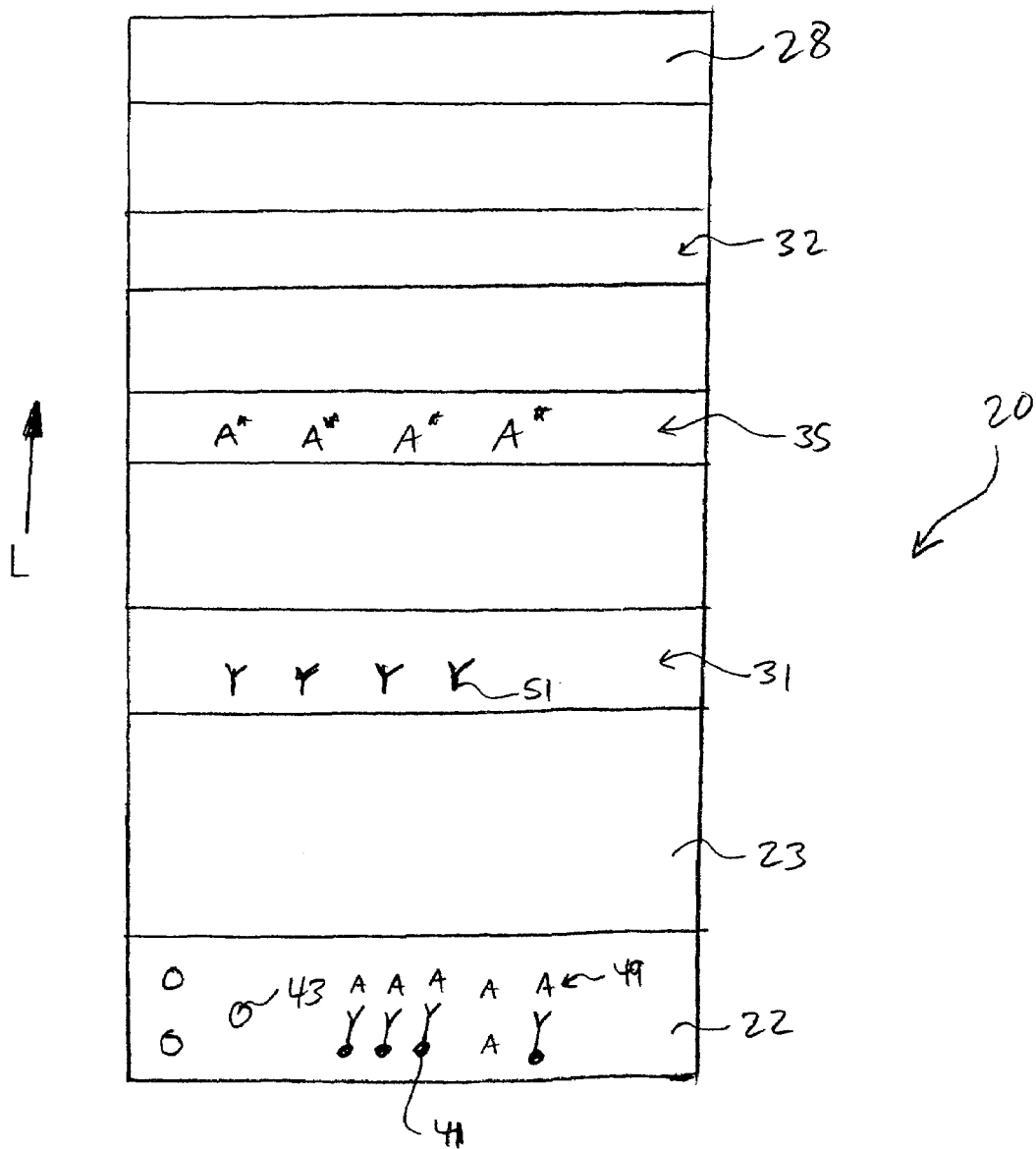
FIG. 3 is a schematic illustration of the mechanism used for one embodiment of the present invention prior to performance of the assay.
Figure 4:
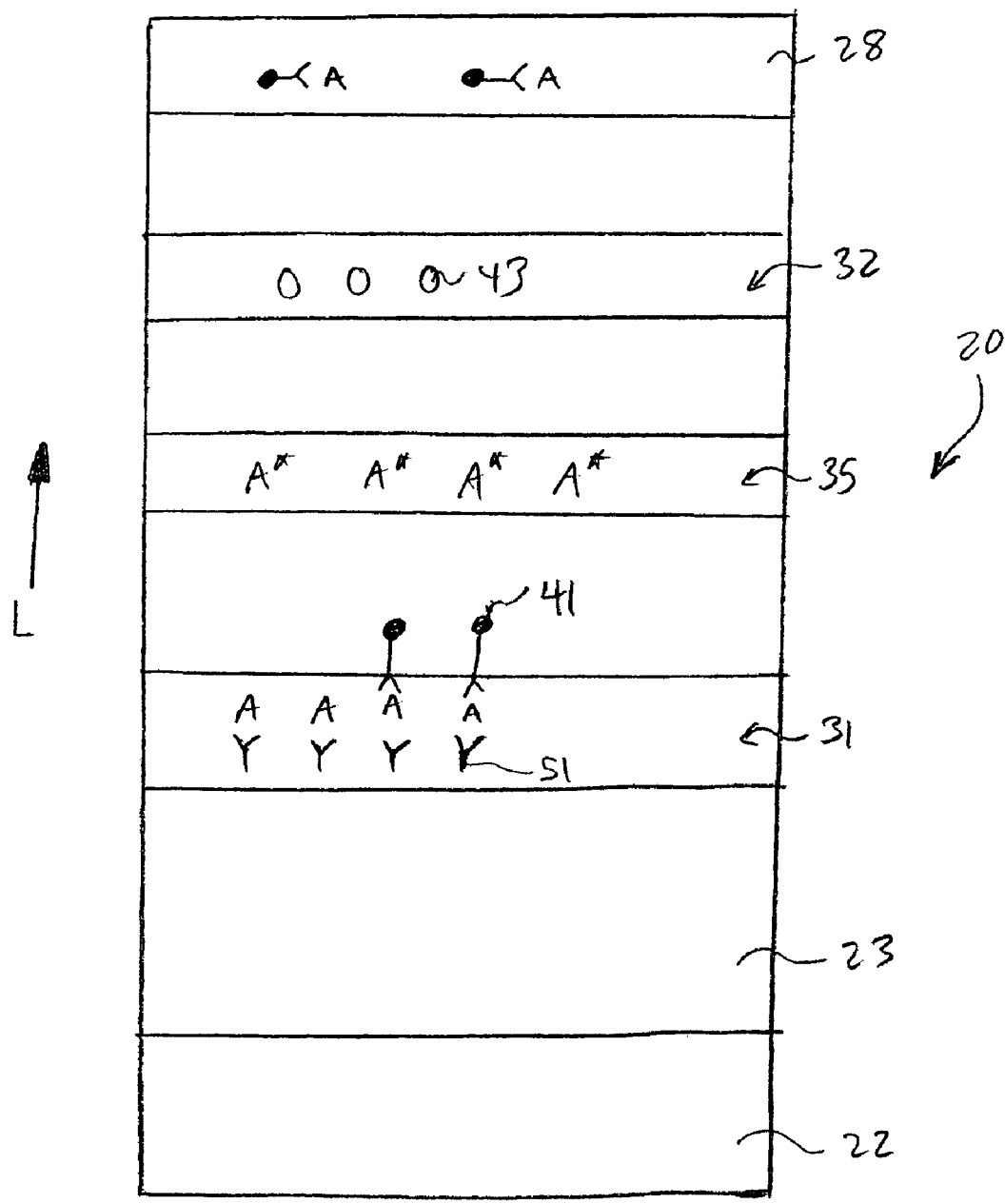
FIG. 4 illustrates the embodiment of FIG. 3 after completion of the assay.

Referring to FIGS. 3-4, one particular embodiment of a method for detecting the presence of an excess concentration of antigen will now be described in more detail. Initially, as shown in FIG. 3, a test sample containing an antigen A is applied to the sample pad (not shown) and travels in the direction "L" to the conjugate pad 22, where the analyte A mixes with detection probes 41 conjugated with an antibody and calibration probes 43 conjugated with biotin (i.e., "biotinylated"). In the embodiment illustrated in FIG. 3, the antigen A binds with the conjugated detection probes 41 to form analyte/conjugated probe complexes 49. Some of the antigen A remains free due to the limited availability of the conjugated detection probes 41. As shown in FIG. 4, the free antigen A and the complexes 49 then travel to the detection zone 31, within which is immobilized an antibody 51. The free antigen A and the complexes 49 compete for binding sites on the immobilized antibody 51. Any remaining antigen A and complexes 49 travel to the indicator zone 35, within which is immobilized a molecule A* that is identical in nature to the antigen A. However, because the antigen A and complexes 49 do not possess a site for binding to the molecule A*, they generally pass through the indicator zone 35 until they reach the absorbent pad 28. Finally, the biotinylated calibration probes 43 travel through both the detection zone 31 and indicator zone 35 to bind with streptavidin (not shown), which is immobilized within the calibration zone 32. The intensity of the signals produced by any detection probes 41 captured at the detection zone 31 and the indicator zone 35 may then be measured. In addition, the intensity of the signal produced by the calibration probes 43 at the calibration zone 32 may also be measured, and should generally remain constant for any analyte concentration.

If desired, an optical reader may be used in some embodiments to measure the intensity of the probes. The actual configuration and structure of the optical reader may generally vary as is readily understood by those skilled in the art. For example, optical detection techniques that may be utilized include, but are not limited to, luminescence (e.g., fluorescence, phosphorescence, etc.), absorbance (e.g., fluorescent or non-fluorescent), diffraction, etc. One suitable reflectance spectrophotometer is described, for instance, in U.S. Patent App. Pub. No. 2003/0119202 to Kaylor, et al., which is incorporated herein in its entirety by reference thereto for all purposes. In another embodiment, a reflectance-mode spectrofluorometer may be used to detect the presence of probes that exhibit fluorescence. Suitable spectrofluorometers and related detection techniques are described, for instance, in U.S. Patent App. Pub. No. 2004/0043502 to Song, et al., which is incorporated herein in its entirety by reference thereto for all purposes. Likewise, a transmission-mode detection system may also be used to detect the presence of detection probes.

Typically, the optical reader contains an illumination source that is capable of emitting electromagnetic radiation and a detector that is capable of registering a signal (e.g., transmitted or reflected light, emitted fluorescence or phosphorescence, etc.). The illumination source may be any device known in the art that is capable of providing electromagnetic radiation, such as light in the visible or near-visible range (e.g., infrared or ultraviolet light). For example, suitable illumination sources that may be used in the present invention include, but are not limited to, light emitting diodes (LED), flashlamps, cold-cathode fluorescent lamps, electroluminescent lamps, and so forth. The illumination may be multiplexed and/or collimated. In some cases, the illumination may be pulsed to reduce any background interference.

Further, illumination may be continuous or may combine continuous wave (CW) and pulsed illumination where multiple illumination beams are multiplexed (e.g., a pulsed beam is multiplexed with a CW beam), permitting signal discrimination between a signal induced by the CW source and a signal induced by the pulsed source. For example, in some embodiments, LEDs (e.g., aluminum gallium arsenide red diodes, gallium phosphide green diodes, gallium arsenide phosphide green diodes, or indium gallium nitride violet/blue/ultraviolet (UV) diodes) are used as the pulsed illumination source. One commercially available example of a suitable UV LED excitation diode suitable for use in the present invention is Model NSHU55OE (Nichia Corporation), which emits 750 to 1000 microwatts of optical power at a forward current of 10 milliamps (3.5-3.9 volts) into a beam with a full-width at half maximum of 10 degrees, a peak wavelength of 370-375 nanometers, and a spectral half-width of 12 nanometers.

In some cases, the illumination source may provide diffuse illumination to the assay device. For example, an array of multiple point light sources (e.g., LEDs) may simply be employed to provide relatively diffuse illumination. Another particularly desired illumination source that is capable of providing diffuse illumination in a relatively inexpensive manner is an electroluminescent (EL) device. An EL device is generally a capacitor structure that utilizes a luminescent material (e.g., phosphor particles) sandwiched between electrodes, at least one of which is transparent to allow light to escape. Application of a voltage across the electrodes generates a changing electric field within the luminescent material that causes it to emit light.

The detector may generally be any device known in the art that is capable of sensing a signal. For instance, the detector may be an electronic imaging detector that is configured for spatial discrimination. Some examples of such electronic imaging sensors include high speed, linear charge-coupled devices (CCD), charge-injection devices (CID), complementary-metal-oxide-semiconductor (CMOS) devices, and so forth. Such image detectors, for instance, are generally two-dimensional arrays of electronic light sensors, although linear imaging detectors (e.g., linear CCD detectors) that include a single line of detector pixels or light sensors, such as, for example, those used for scanning images, may also be used. Each array includes a set of known, unique positions that may be referred to as "addresses." Each address in an image detector is occupied by a sensor that covers an area (e.g., an area typically shaped as a box or a rectangle). This area is generally referred to as a "pixel" or pixel area. A detector pixel, for instance, may be a CCD, CID, or a CMOS sensor, or any other device or sensor that detects or measures light. The size of detector pixels may vary widely, and may in some cases have a diameter or length as low as 0.2 micrometers.

In other embodiments, the detector may be a light sensor that lacks spatial discrimination capabilities. For instance, examples of such light sensors may include photomultiplier devices, photodiodes, such as avalanche photodiodes or silicon photodiodes, and so forth. Silicon photodiodes are sometimes advantageous in that they are inexpensive, sensitive, capable of high-speed operation (short risetime/high bandwidth), and easily integrated into most other semiconductor technology and monolithic circuitry. In addition, silicon photodiodes are physically small, which enables them to be readily incorporated into a system for use with a membrane-based device. If silicon photodiodes are used, then the wavelength range of the emitted signal may be within their range of sensitivity, which is 400 to 1100 nanometers.

Figure 2:
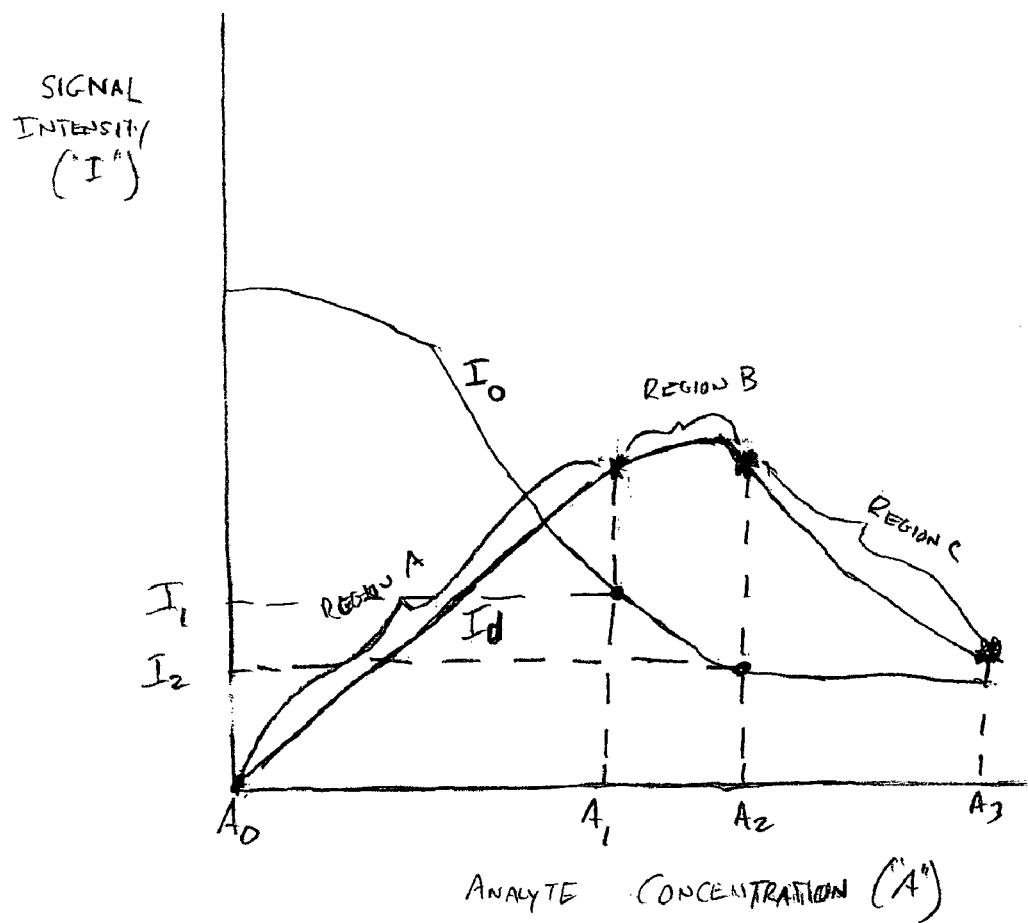
FIG. 2 is a graphical illustration of the relationship between analyte concentration and signal intensities for the detection and indicator zones in accordance with one embodiment of the present invention.

Generally speaking, qualitative, quantitative, or semi-quantitative determination of the presence or concentration of an analyte may be achieved in accordance with the present invention. For example, as stated above, the amount of the analyte may be quantitatively or semi-quantitatively determined by using the intensities of the signals produced by probes captured at the detection zone 31 and the indicator zone 35, and optionally with the intensity signal at the calibration zone 32. The ability to utilize different signal intensities to determine analyte concentration is illustrated graphically in FIG. 2. It should be understood that the signal intensities do not necessarily have to follow the illustrated relationship, and that this relationship is given for exemplary purposes only. In this regard, FIG. 2 show the relationship of the signal intensity of the detection probes of FIGS. 3 and 4 for both the indicator zone 35 and the detection zone 31. For purposes of illustration only, FIG. 2 does not include a calibration signal intensity. However, as discussed above, a calibration signal intensity may be utilized to calibrate the results. For example, the ratio of $I_d$ to $I_c$ versus analyte concentration may be plotted to develop the dose response curve discussed above.

As shown in FIG. 2, when no antigen A is present in the test sample, all of the detection probes 41 bind to the antigen A* within the indicator zone 35 and produce an indicator signal intensity ("$I_o$") that is at a maximum value. The detection zone 31 produces no signal. As its concentration increases, the antigen A begins to form complexes 49 with the conjugated detection probes 41. The complexes 49 possess an epitope capable of binding with the antibody 51 at the detection zone 31. This causes a decrease in the indicator signal intensity "$I_o$", and also causes the production of a detection signal intensity "$I_d$" at the detection zone 31. The intensity of the indicator signal "$I_o$" continues to decrease and the intensity of the detection signal "$I_d$" continues to increase until the concentration of the antigen A exceeds the amount of available conjugated detection probes 41. This is known as the "saturation concentration" of the analyte. At the saturation concentration, the free analyte A and complexes 49 begin to compete for binding sites at the detection zone 31. Accordingly, the intensity of the detection signal "$I_d$" reaches its maximum value. This value is generally known because the amount of detection probes 41 is selected to correspond to the amount of the available antibody 51 at the detection zone 31. As the antigen concentration increases further, the detection signal intensity "$I_d$" begins to decrease due to the escalating presence of free, unlabeled antigen A within the detection zone 31. Moreover, at or near the analyte saturation concentration, no indicator signal intensity will theoretically be detected as all of the detection probes 41 will complex with the analyte A, and subsequently bind to the antibody 51 within the detection zone 31. In practice, however, a small number of detection probes 41 may bind to the antigen A* within the indicator zone 35 such that a relatively low indicator signal intensity "$I_o$" is still produced.

In accordance with the present invention, various regions of the dose response curve of FIG. 2 may be selectively employed to convert a measured detection signal intensity to analyte concentration. For example, "Region A" of the curve is defined between analyte concentrations "$A_o$" and "$A_1$." In this region, the detection signal intensity bears an almost linear relationship with analyte concentration. Thus, "Region A" of FIG. 2 may be used to accurately convert the measured detection signal intensity "$I_d$" to an actual analyte concentration. Likewise, "Region C" defines of the curve is defined between analyte concentrations "$A_2$" and $A_3$." Again, in this region, the detection signal intensity bears an almost linear relationship with analyte concentration. Thus, "Region C" of FIG. 2 may also be used to accurately convert the measured detection signal intensity "$I_d$" to an actual analyte concentration. "Region B" of the detection curve, which is defined between analyte concentrations "$A_1$" and "$A_2$" is relatively constant, and as such, it is sometimes difficult to obtain an accurate correlation to analyte concentration. Thus, if quantitative results are desired, the user may dilute a subsequent test sample and then re-perform the assay. Alternatively, the indicator signal intensity may be used alone or in conjunction with the detection signal intensity to provide a quantitative result. If only semi-quantitative results are desired, the analyte concentration may simply be said to fall within between the range of analyte concentrations "$A_1$" and $A_2$."

To determine which region of the dose response curve of FIG. 2 is most suited for a particular test sample, it is generally desired to first determine whether the analyte concentration is within the "hook effect" region. In this regard, a measured signal intensity "$I_o$" may be compared to a reference standard that is predetermined for a known saturation concentration of the analyte. The "reference standard" may be a single intensity value or it may encompass a range of values that are believed to correspond to the saturation concentration within a certain margin of error. The upper and lower limit of the range of values may be selected based on the extent the indicator signal intensity varies over multiple test runs for the same known analyte saturation concentration. For example, in FIG. 2, the reference standard may be defined between intensity values "$I_1$" and "$I_2$", which correspond to analyte concentrations "$A_1$" and "$A_2$", respectively. A measured signal intensity "$I_o$" that is greater than the reference standard (e.g., greater than the upper limit "$I_1$") serves as an indicator that the analyte concentration is outside of the "hook effect" region, while a measured signal intensity "$I_o$" that is the same or less than the reference standard (e.g., less than the upper limit "$I_1$") serves as an indicator that the analyte concentration is within the "hook effect" region.

Figure 5:
FIG. 5 illustrates one embodiment of a method for determining whether an analyte concentration is within the "hook effect" region, and for semi-quantitatively or quantitatively determining the analyte concentration.
Figure 5:
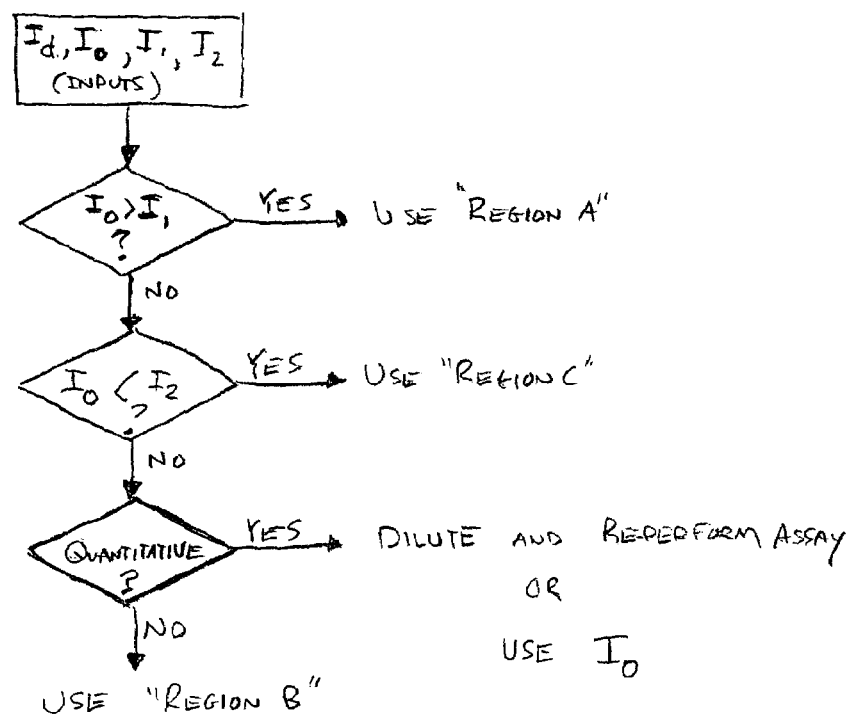

Referring to FIG. 5, for instance, one embodiment of a method 100 is shown for determining whether the analyte concentration is within the "hook effect" region. Several variables are used as inputs in the method 100, including the measured detection signal intensity "$I_d$", the measured indicator signal intensity "$I_o$", and the upper limit $I_1$ and lower limit $I_2$ of the reference standard. The first step of the method 100 is to determine whether the measured signal intensity "$I_o$" is greater than the upper limit "$I_1$". If so, the analyte concentration is outside the "hook effect" region, and "Region A" of the dose response curve may be used to convert the measured detection signal intensity "$I_d$" to an analyte concentration. If the measured signal intensity "$I_o$" is less than the upper limit "$I_1$", the next step of the method 100 is to determine whether the analyte concentration is at or near the saturation concentration, or if it is well above the saturation concentration. Thus, the method 100 determines whether the measured signal intensity "$I_o$" is less than the lower limit "$I_2$", and if so, "Region C" of the dose response curve may be used to convert the measured detection signal intensity "$I_d$" to an analyte concentration. If the measured signal intensity "$I_o$" is greater than the lower limit "$I_2$" but less than the upper limit "$I_1$" (i.e., the same as the reference standard), the final step of the method 100 is to determine whether semi-quantitative or quantitative results are desired. If quantitative results are desired, the method 100 instructs the user to dilute a subsequent test sample and then re-perform the assay. Alternatively, the measured indicator signal intensity "$I_o$" may also be used alone, or in conjunction with the detection signal intensity "$I_d$" to provide quantitative results. For example, as shown in FIG. 2, the indicator curve is relatively linear within "Region B" of the detection signal curve. Thus, within this region, the indicator curve may provide accurate detection results. Moreover, if only semi-quantitative results are desired, the method 100 simply indicates that the analyte concentration falls within the range of analyte concentrations "$A_1$" and "$A_2$" shown in FIG. 2.

Correlation methods, such as described above, may be performed automatically and/or manually. For example, a microprocessor may optionally be employed to automatically select the desired correlation technique and to convert the measurement from the detector to a result that quantitatively or semi-quantitatively indicates the concentration of the analyte. The microprocessor may include memory capability to allow the user to recall the last several results. Those skilled in the art will appreciate that any suitable computer-readable memory devices, such as RAM, ROM, EPROM, EEPROM, flash memory cards, digital video disks, Bernoulli cartridges, and so forth, may be used. If desired, the results may be conveyed to a user using a liquid crystal (LCD) or LED display.

The present invention may be better understood with reference to the following examples.

EXAMPLE 1

The ability to form a lateral flow assay device was demonstrated. A nitrocellulose porous membrane (HF 120 from Millipore, Inc.) having a length of approximately 30 centimeters was laminated onto supporting cards. Monoclonal antibody for C-reactive protein was immobilized on the porous membrane to form a detection zone. The antibody was obtained from BiosPacific, Inc. (Catalog #A58040136P) and had a concentration of 1 milligram per milliliter. CRP antigen was immobilized on the porous membrane to form an indicator zone. The antigen was obtained from Biogenesis Inc. of Kingston, N.H., and had a concentration of 2.78 milligrams per milliliter. Goldline™ (a polylysine solution obtained from British Biocell International) was striped onto the membrane to form a control zone. The indicator zone was positioned between the detection zone and the control zone. A cellulose wicking pad (Millipore Co.) was laminated with one end (closer to the control zone) of the membrane. The membrane samples were then dried for 1 hour at a temperature of 37° C.

A particle suspension was formed by mixing 180 microliters of gold particles conjugated with monoclonal antibody for CRP (BiosPacific, Inc., Catalog #A58110228P), 375 microliters of sucrose in water (20%) and 945 microliters of water. The gold particles had a particle size of 40 nanometers and an optical density of 56, and were obtained from British Biocell International. The suspension was loaded onto a 25-centimeter long glass fiber conjugate pad (Millipore Co.). The glass fiber pad was dried at 37° C. for 2 hours to form a conjugate pad. The conjugate pad was then laminated onto the other end (closer to the detection zone) of the porous membrane. A cellulose wicking pad (Millipore Co.) sample pad was further laminated onto the conjugate pad. The laminated full card was then cut into a 4-millimeter wide lateral flow assay device.

EXAMPLE 2

Lateral flow devices were formed as described in Example 1, except that 2.23 milligrams per milliliter of goat anti mouse IgG ($F_c$) was used to form the control zone.

EXAMPLE 3

The ability to form a lateral flow assay device was demonstrated. A nitrocellulose porous membrane (HF 120 from Millipore, Inc.) having a length of approximately 30 centimeters was laminated onto supporting cards. Monoclonal antibody for C-reactive protein (BiosPacific, Inc., Catalog #A58040136P) in 0.1% trehalose aqueous solution was immobilized on the porous membrane to form a detection zone. CRP antigen was immobilized on the porous membrane to form an indicator zone. The antigen was obtained from Biogenesis Inc. of Kingston, N.H., and had a concentration of 2.78 milligrams per milliliter. Goat anti alkaline phosphatase (2.5 milligrams per milliliter, obtained from Fitzgerald Industries International, Inc. of Concord, Mass.) was striped onto the membrane to form a calibration zone. The indicator zone was positioned between the detection zone and the calibration zone. A cellulose wicking pad (Millipore Co.) was laminated with one end (closer to the control zone) of the membrane. The membrane samples were then dried for 1 hour at a temperature of 37° C.

160 microliters of gold particles conjugated with Rabbit anti Goat IgG, 160 microliters of gold particles conjugated with CRP monoclonal antibody (BiosPacific, Inc., Catalog #A58110228P), 375 microliters of sucrose in water (20%), and 785 microliters of water were mixed to form a particle suspension. The gold particles conjugated with Rabbit anti Goat IgG had a particle size of 10 nanometers, and were obtained from Sigma-Aldrich, Inc. of St. Louis, Mo. The gold particles conjugated with CRP monoclonal antibody had a particle size of 40 nanometers, and were obtained from British Biocell International. The suspension was loaded onto a 20-centimeter long glass fiber conjugate pad (Millipore Co.). The glass fiber pad was dried at 37° C. for 2 hours to form a conjugate pad. The conjugate pad was laminated onto the other end (closer to the detection zone) of the porous membrane. A cellulose wicking pad (Millipore Co.) sample pad was further laminated onto the conjugate pad. The laminated full card was then cut into a 4-millimeter wide lateral flow assay device.

EXAMPLE 4

The ability to detect the presence and quantity of an analyte using the lateral flow assay devices of Example 1 was demonstrated. Eleven (11) of the assay devices were tested. 120 microliters of C-reactive protein in TBS buffer were applied to the sample pad of each device. Different concentrations of CRP were tested, i.e., 0; 10; 50; 200; 500; 1,000; 2,000; 5,000; 20,000; 100,000; and 500,000 nanograms per milliliter. The devices were allowed to develop for 30 minutes. The color intensity of each zone on each device was measured using a reflectance-based spectrophotometer. The intensity at each zone is summarized in Table 1.

TABLE 1

| CRP (ng/ml) | Intensity for CRP Concentrations | | |
| --- | --- | --- | --- |
| | Detection zone | Indicator zone | Control zone |
| 0 | 103.579 | 124.137 | 109.493 |
| 10 | 117.739 | 125.202 | 112.447 |
| 50 | 124.030 | 123.561 | 112.375 |
| 200 | 126.612 | 118.932 | 112.715 |
| 500 | 126.806 | 112.629 | 112.543 |
| 1,000 | 127.710 | 112.268 | 115.873 |
| 2,000 | 126.652 | 110.438 | 119.687 |

TABLE 1-continued

| | Intensity for CRP Concentrations | | |
|---|---|---|---|
| CRP (ng/ml) | Detection zone | Indicator zone | Control zone |
| 5,000 | 121.435 | 107.235 | 122.621 |
| 20,000 | 115.403 | 105.377 | 122.614 |
| 100,000 | 111.264 | 104.776 | 121.352 |
| 500,000 | 109.519 | 105.772 | 122.566 |

Figure 6:
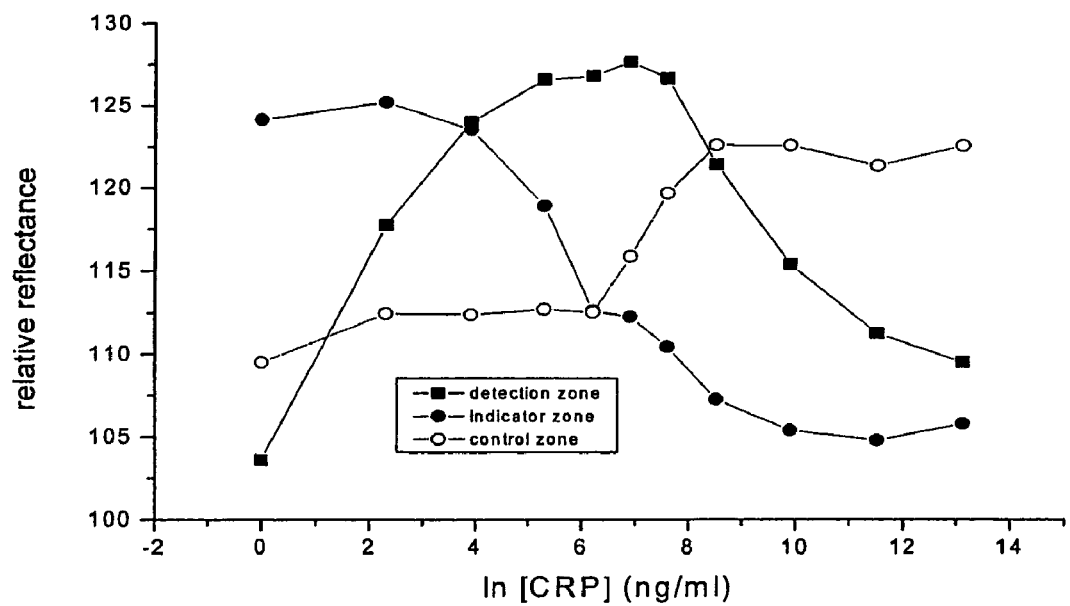
FIG. 6 is the dose response curve for Example 4 in which signal intensity is plotted versus CRP concentration.

The intensities are plotted versus CRP concentration in FIG. 6. As shown, the indicator zone is capable of predicting whether the CRP concentration is within the "hook effect" region.

EXAMPLE 5

The ability to detect the presence and quantity of an analyte using the lateral flow assay devices of Example 2 was demonstrated. Eleven (11) of the assay devices were tested. 120 microliters of C-reactive protein in TBS buffer were applied to the sample pad of each device. Different concentrations of CRP were tested, i.e., 0; 10; 50; 200; 500; 1,000; 2,000; 5,000; 20,000; 100,000; and 500,000 nanograms per milliliter. The devices were allowed to develop for 30 minutes. The color intensity of each zone on each device was measured using a reflectance-based spectrophotometer. The intensity at each zone is summarized in Table 2.

TABLE 2

| | Intensity for CRP Concentrations | | |
|---|---|---|---|
| CRP (ng/ml) | Detection zone | Indicator zone | Control zone |
| 0 | 100.349 | 117.180 | 107.962 |
| 10 | 112.441 | 116.806 | 108.131 |
| 50 | 115.145 | 113.111 | 107.717 |
| 200 | 117.522 | 108.417 | 108.247 |
| 500 | 119.923 | 109.125 | 110.521 |
| 1,000 | 122.628 | 110.936 | 119.501 |
| 2,000 | 121.988 | 110.253 | 124.617 |
| 5,000 | 117.599 | 107.891 | 125.062 |
| 20,000 | 112.510 | 106.006 | 123.860 |
| 100,000 | 107.082 | 104.421 | 121.370 |
| 500,000 | 102.879 | 101.487 | 117.520 |

Figure 7:
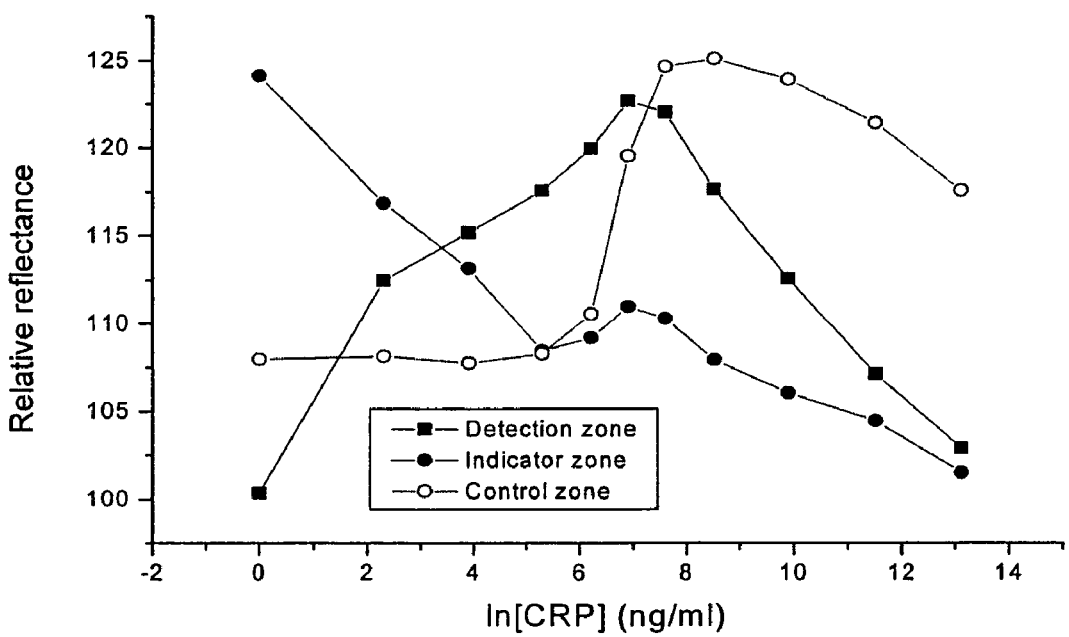
FIG. 7 is the dose response curve for Example 5 in which signal intensity is plotted versus CRP concentration.

The intensities are plotted versus CRP concentration in FIG. 7. As shown, the indicator zone is capable of predicting whether the CRP concentration is within the "hook effect" region.

EXAMPLE 6

The ability to detect the presence and quantity of an analyte using the lateral flow assay devices of Example 3 was demonstrated. Eleven (11) of the assay devices were tested. 120 microliters of C-reactive protein in TBS buffer were applied to the sample pad of each device. Different concentrations of CRP were tested, i.e., 0; 10; 50; 200; 500; 1,000; 2,000; 5,000; 20,000; 100,000; and 500,000 nanograms per milliliter. The devices were allowed to develop for 30 minutes. The color intensity of each zone on each device was measured using a reflectance-based spectrophotometer. The intensity at each zone is summarized in Table 3.

TABLE 3

| | Intensity for CRP Concentrations | | |
|---|---|---|---|
| CRP (ng/ml) | Detection zone | Indicator zone | Calibration zone |
| 0 | 0.0000 | 2.4660 | 0.3537 |
| 10 | 0.6791 | 3.0580 | 0.3354 |
| 50 | 1.8680 | 2.1970 | 0.2652 |
| 200 | 2.4970 | 1.8590 | 0.2746 |
| 500 | 2.2970 | 1.7490 | 0.2691 |
| 1,000 | 2.1910 | 1.6990 | 0.3809 |
| 2,000 | 1.1770 | 1.3200 | 0.2277 |
| 5,000 | 0.7312 | 0.1133 | 0.3000 |
| 20,000 | 0.3121 | 0.0000 | 0.2329 |
| 100,000 | 0.2133 | 0.0000 | 0.2355 |
| 500,000 | 0.1938 | 0.0000 | 0.2478 |

Figure 8:
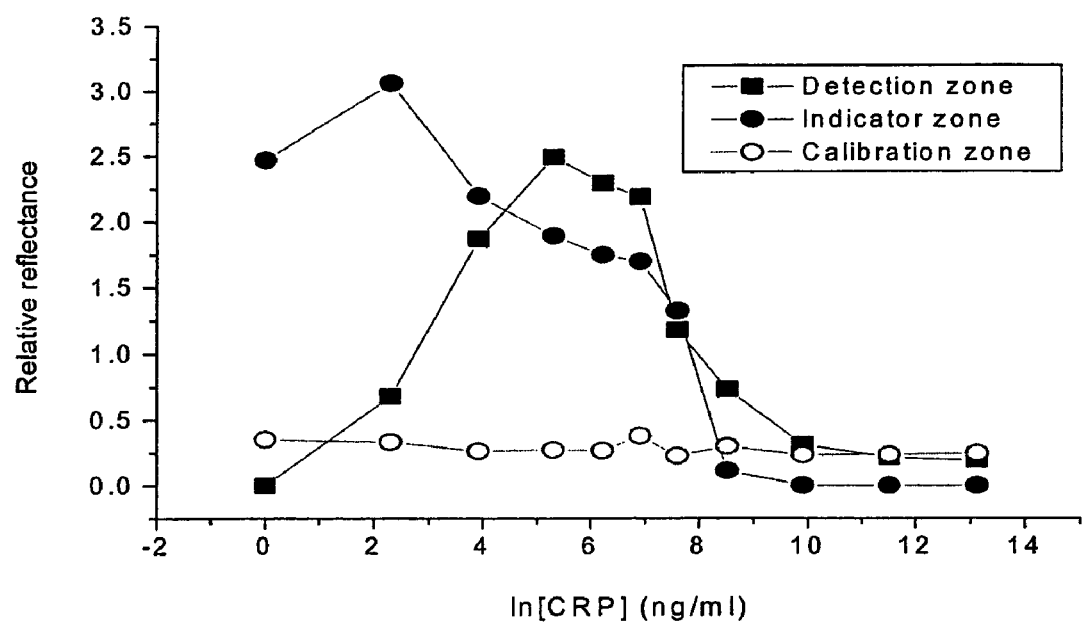
FIG. 8 is the dose response curve for Example 6 in which signal intensity is plotted versus CRP concentration.

The intensities are plotted versus CRP concentration in FIG. 8. As shown, the indicator zone is capable of predicting whether the CRP concentration is within the "hook effect" region.

EXAMPLE 7

The ability to vary the detection sensitivity of an assay device was demonstrated. A particle suspension was initially formed by diluting gold particles conjugated with monoclonal antibody for CRP (BiosPacific, Inc., Catalog #A58110228P) in 2 millimolar Borax (pH of 7.2) to a concentration at which the optical density was 10. The gold particles had a particle size of 40 nanometers. The suspension was sprayed at a rate of 25 microliters per second (5 μl/cm, 5 cm/s) onto a 34-millimeter long glass fiber conjugate pad (Millipore Co.) using a "Kinematic 1600" reagent dispensing module (Kinematic Automation, Inc. of Twain Harte, Calif.). The glass fiber pad was allowed to dry overnight at room temperature and a relative humidity of less than 20%.

The conjugate pad was then laminated onto an end of a nitrocellulose porous membrane (HF 180 from Millipore, Inc.) having a length of approximately 30 centimeters. Monoclonal antibody for C-reactive protein (BiosPacific, Inc., Catalog #A58110228P) was diluted to concentrations of 0.2 and 0.3 milligrams per milliliter in PBS buffer. CRP antigen was also obtained from Biogenesis Inc. of Kingston, New Hampshire and diluted to a concentration of 3.4 milligrams per milliliter in TBS buffer. The reagents were striped at rates of 5 microliters per second (1 μL/cm, 5 cm/s) onto the porous membrane using a "Kinematic 1600" reagent dispensing module (Kinematic Automation, Inc. of Twain Harte, Calif.). The immobilized monoclonal antibody formed a detection zone positioned 10 millimeters from an edge of the membrane. The immobilized CRP antigen formed an indicator zone positioned 10 millimeters from the other edge of the membrane and 5 millimeters downstream from the detection zone. A CF6 cellulose/glass wicking pad (Whatman plc of Middlesex, United Kingdom) was cut to a width of 20 millimeters and laminated to the nitrocellulose membrane. The laminated card was then cut into 4-mm wide, full lateral flow dipsticks.

The resulting assay devices were placed into a housing (holds 14 dipsticks) and striped by hand using a positive displacement pipette with 1 microliter of calibrated CRP sera (0 to 480 micrograms per milliliter) obtained from Kamiya Biomedical Co. of Seattle, Wash. This stripe of sera was placed at the point 12 mm from the edge of the GF 33 pad. The assay devices were tested by applying 110 microliters PBS buffer (pH 7.2 with 2% Tween 20) upstream from the point of sera application, in order to wash or "chase" the sera along the test strip. The devices were allowed to develop for 30 minutes. The color intensity of each zone on each device was determined using a visual scale ("Rann scale") ranging from 0-11, wherein 0 represents no color and 11 represents the most intense color. The intensity of each zone is summarized in Tables 4 and 5.

TABLE 4

Intensity of Zones for Detection Antibody Concentration of 0.2 mg/ml

| CRP Conc. | Detection Zone | | Indicator Zone | |
| --- | --- | --- | --- | --- |
| | Initial | 30 minutes | Initial | 30 minutes |
| 0.0 | 5 | 6 | 10 | 10 |
| 0.5 | 7 | 8 | 10 | 10 |
| 1.5 | 10 | 10 | 10 | 10 |
| 2.5 | 10 | 10 | 10 | 10 |
| 5.0 | 10 | 10 | 9 | 9 |
| 7.5 | 10 | 10 | 8 | 8 |
| 10.0 | 10 | 10 | - | 8 |
| 20.0 | 10 | 10 | 8 | 8 |
| 48.0 | 8 | 9 | 6 | 5 |
| 80.0 | 6 | 6 | 2 | 2 |
| 160.0 | 4 | 4 | 0 | 0 |
| 480.0 | 2 | 2 | 0 | 0 |

TABLE 5

Intensity of Zones for Detection Antibody Concentration of 0.3 mg/ml

| CRP Conc. | Detection Zone | | Indicator Zone | |
| --- | --- | --- | --- | --- |
| | Initial | 30 minutes | Initial | 30 minutes |
| 0.0 | 4 | 0 | 11 | 11 |
| 0.5 | 9 | 9 | 11 | 11 |
| 1.5 | 10 | 10 | 10 | 10 |
| 2.5 | 11 | 11 | 9 | 9 |
| 5.0 | 11 | 11 | 9 | 9 |
| 7.5 | 11 | 11 | 9 | 8.5 |
| 10.0 | 11 | 11 | 8 | 8 |
| 20.0 | 10 | 10 | 5 | 5 |
| 48.0 | 9 | 9 | 3 | 3 |
| 80.0 | 9 | 8 | 2 | 2 |
| 160.0 | 6 | 6 | 0.5 | 0.5 |
| 480.0 | 3 | 3 | 0 | 0 |

As indicated above, the concentration of the antibody used in the detection zone may be varied to provide different detection sensitivities. In this manner, the antibody concentration may be selectively controlled to generate a dose response curve within a sensitivity range that is believed to better correspond to the test conditions. For example, the antibody concentration may be adjusted so that the linear region of the dose response curve exists at a higher analyte concentration.

EXAMPLE 8

The ability to vary the detection sensitivity of an assay device was demonstrated. Particle suspensions were initially formed by diluting gold particles conjugated with monoclonal antibody for CRP (BiosPacific, Inc., Catalog #A58110228P) in 2 millimolar Borax (pH of 7.2) to a concentration at which the optical density was 5, 8,10, 12, 15, 18, or 20. The gold particles had a particle size of 40 nanometers. The suspensions were sprayed at a rate of 25 microliters per second (5 µL/cm, 5 cm/s) onto a 34-millimeter long glass fiber conjugate pad (Millipore Co.) using a "Kinematic 1600" reagent dispensing module (Kinematic Automation, Inc. of Twain Harte, Calif.). The glass fiber pad was allowed to dry overnight at room temperature and a relative humidity of less than 20%.

The conjugate pad was then laminated onto an end of a nitrocellulose porous membrane (HF 180 from Millipore, Inc.) having a length of approximately 30 centimeters. Monoclonal antibody for C-reactive protein (BiosPacific, Inc., Catalog #A58110228P) was diluted to a concentration of 0.1 milligrams per milliliter in PBS buffer. CRP antigen was also obtained from Biogenesis Inc. of Kingston, N.H. and diluted to a concentration of 3.4 milligrams per milliliter in TBS buffer. The reagents were striped at rates of 5 microliters per second (1 µL/cm, 5 cm/s) onto the porous membrane using a "Kinematic 1600" reagent dispensing module (Kinematic Automation, Inc. of Twain Harte, Calif.). The immobilized monoclonal antibody formed a detection zone positioned 10 millimeters from an edge of the membrane. The immobilized CRP antigen formed an indicator zone positioned 10 millimeters from the other edge of the membrane and 5 millimeters downstream from the detection zone. A CF6 cellulose/glass wicking pad (Whatman plc of Middlesex, United Kingdom) was cut to a width of 20 millimeters and laminated to the nitrocellulose membrane. The laminated card was then cut into 4-mm wide, full lateral flow dipsticks.

The resulting assay devices were placed into a housing (holds 14 dipsticks) and striped by hand using a positive displacement pipette with 1 microliter of calibrated CRP sera (0 to 480 micrograms per milliliter) obtained from Kamiya Biomedical Co. of Seattle, Wash. This stripe of sera was placed at the point 12 mm from the edge of the GF 33 pad. The assay devices were tested by applying 110 microliters of PBS buffer (pH 7.2 with 2% Tween 20) upstream from the point of sera application, in order to wash or "chase" the sera along the test strip. The devices were allowed to develop for 30 minutes. The color intensity of each zone on each device was measured using the above-described "Rann" scale. The results are shown in FIGS. 9-10.

Figure 9:
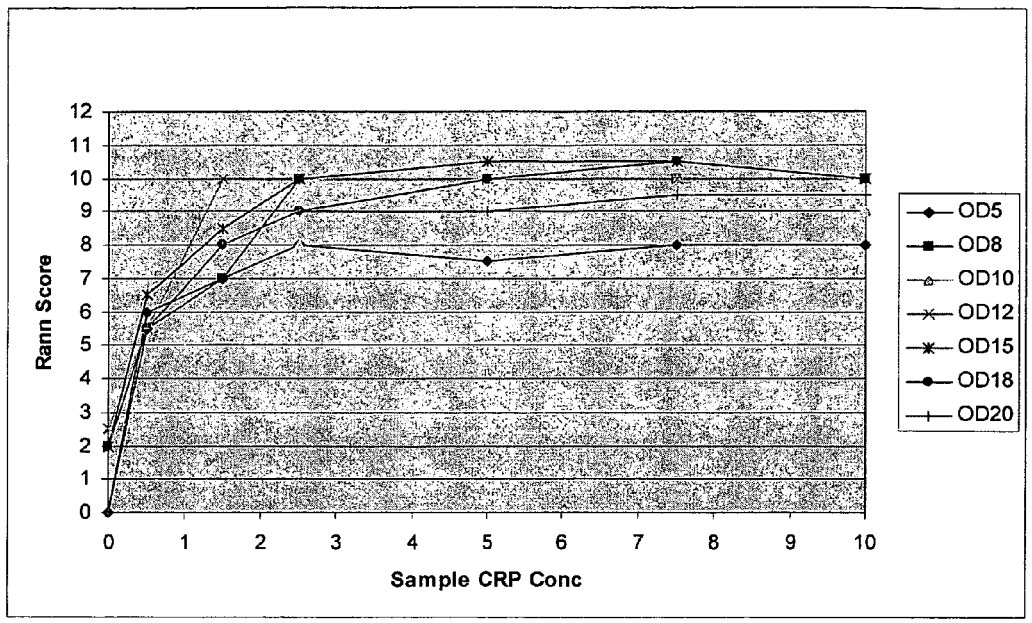
FIG. 9 is the dose response curve for each conjugate particle concentration of Example 8 in which the intensity (i.e., Rann score) produced by the detection zone is plotted versus CRP concentration.
Figure 10:
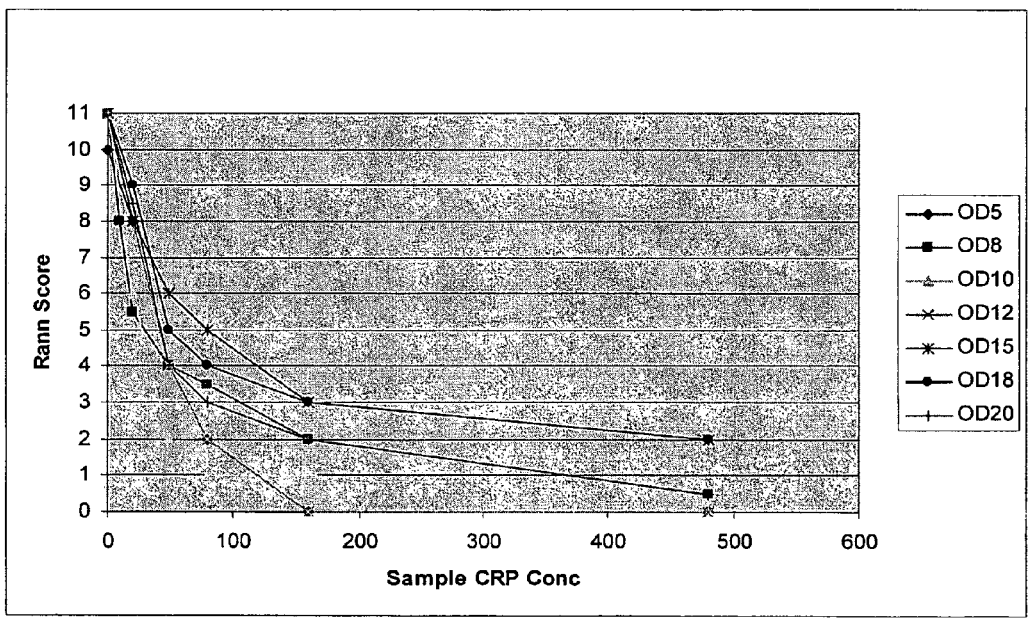
FIG. 10 is the dose response curve for each conjugate particle concentration of Example 8 in which the intensity (i.e., Rann score) produced by the indicator zone is plotted versus CRP concentration.

As shown in FIG. 9, the antibody response curve ("detection zone") and the signal intensities (e.g., "Rann" values) can be varied by altering conjugate particle concentration (as reflected by optical density). Similarly, as shown in FIG. 10, the CRP response curve ("indicator zone") and signal intensities can also be varied by altering conjugate particle concentration. Thus, as indicated, the concentration of the conjugated particles may be selectively controlled to generate a dose response curve within a sensitivity range that is believed to better correspond to the test conditions.

EXAMPLE 9

The ability to vary the detection sensitivity of an assay device was demonstrated. Half-stick assay devices were made for initial experiments. Two solutions of monoclonal antibody for CRP (BiosPacific, Inc., Catalog #A58110228P) were prepared by diluting the antibody stock solution in PBS 0/0 to give 0.1 and 0.5 milligram per milliliter concentrations. Each solution was then striped onto separate nitrocellulose membranes (HF 120 from Millipore, Inc.) having a length of approximately 30 centimeters. The solutions were striped at a rate of 5 microliters per second (1 µl/cm dispense rate with 5 cm/sec bed speed) using a "Kinematic 1600" reagent dispensing module (Kinematic Automation, Inc. of Twain Harte, Calif.). A solution of CRP (from Biogenesis Inc. of Kingston, N.H.), diluted to 0.5 mg/mL in PBS 0/0 (pH of 7.2), was also striped onto the card using the Kinematic 1600. The cards were left to dry at 37° C. for 1 hour, and laminated with a 20-millimeter wide cellulosic fiber wick (Millipore CFSP203000). The cards were cut to 4-millimeter wide strips using a "Kinematic 2360" slitter (Kinematic Automation, Inc. of Twain Harte, Calif.), resulting in 4-millimeter wide half lateral flow dipsticks ("half-sticks").

For testing, particle suspensions of varying sizes of gold particles previously conjugated with monoclonal antibody for CRP (BiosPacific, Inc., Catalog #A58110228P) were used. The sizes studied in this example were 40 and 60 nanometer diameter gold particle conjugates. The particle conjugates were diluted in TBS 1/0/1 to the desired optical density (OD) for testing, i.e., OD 1 and OD 2.5. CRP standards from Scipac were diluted in PBS 0/0 to a concentration range of 0-40 micrograms per milliliter, such that once mixed with an equal volume of the gold conjugate, they would result in a testing range of 0 to 20 micrograms per milliliter of CRP. 20 microliters of the CRP solution and 20 microliters of the gold conjugate suspension were added to a 96-well plate. The half-stick samples were then placed in the well, and the tests were allowed to run for 15 minutes prior to visual scoring of the resulting test lines. Visual scoring of the color intensity of each zone on each device was conducted using a "Rann scale" ranging from 0 (no visible color on the test line) to 11 (very intense color on the test line).

Figure 11:
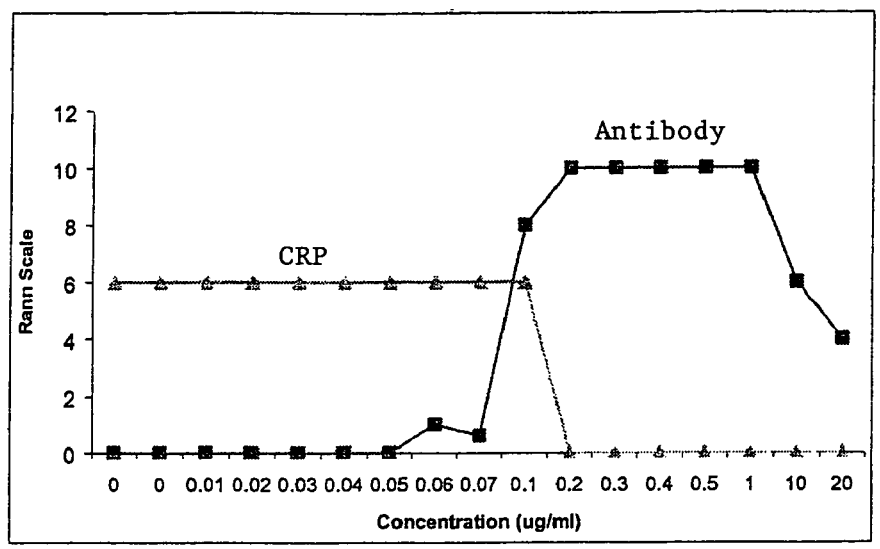
FIG. 11 is the dose response curve for Example 9 in which the Rann score of the detection zone and indicator zone are plotted versus CRP concentration for a gold particle size of 40 nanometers, a conjugate optical density of 1.0, an antibody line concentration of 0.5 milligrams per milliliter, and a CRP line concentration of 0.5 milligrams per milliliter.
Figure 12:
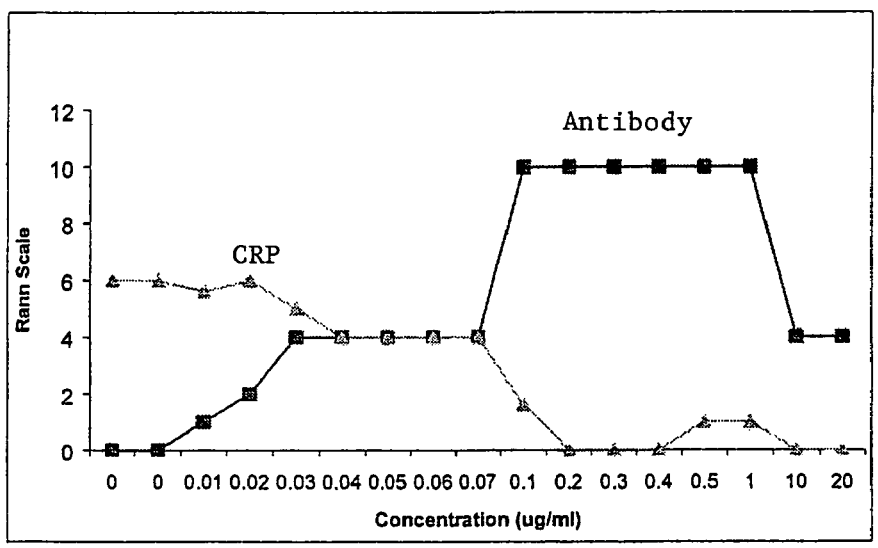
FIG. 12 is the dose response curve for Example 9 in which the Rann score of the detection zone and indicator zone are plotted versus CRP concentration for a gold particle size of 60 nanometers, a conjugate optical density of 1.0, an antibody line concentration of 0.5 milligrams per milliliter, and a CRP line concentration of 0.5 milligrams per milliliter.
Figure 13:
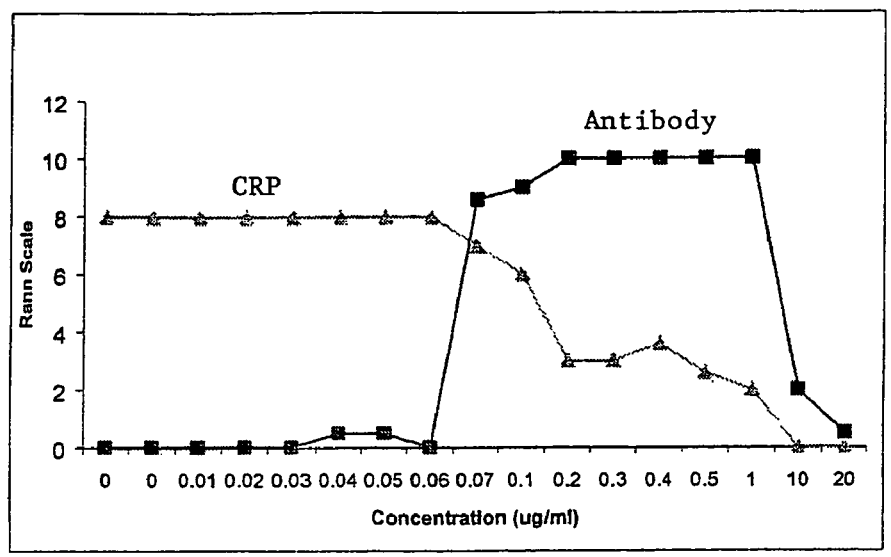
FIG. 13 is the dose response curve for Example 9 in which the Rann score of the detection zone and indicator zone are plotted versus CRP concentration for a gold particle size of 40 nanometers, a conjugate optical density of 1.0, an antibody line concentration of 0.1 milligrams per milliliter, and a CRP line concentration of 0.5 milligrams per milliliter.
Figure 14:
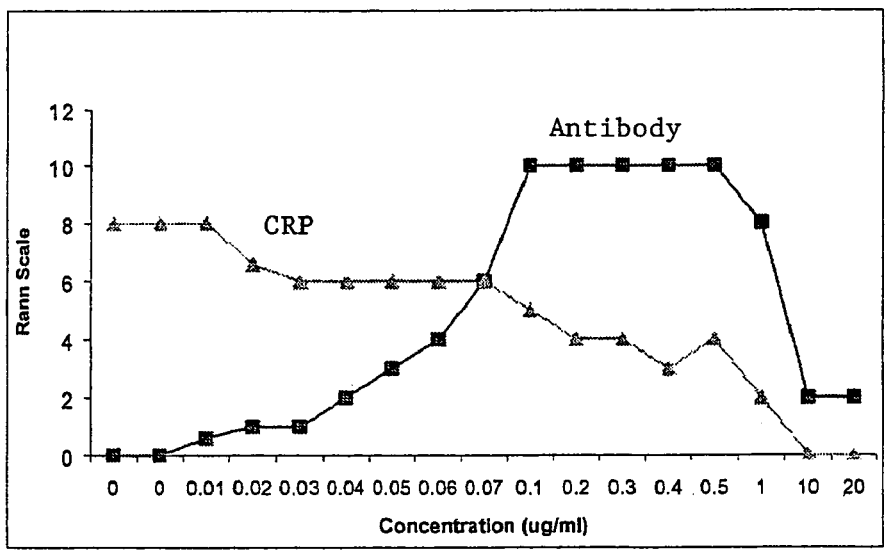
FIG. 14 is the dose response curve for Example 9 in which the Rann score of the detection zone and indicator zone are plotted versus CRP concentration for a gold particle size of 60 nanometers, a conjugate optical density of 1.0, an antibody line concentration of 0.5 milligrams per milliliter, and a CRP line concentration of 0.5 milligrams per milliliter.
Figure 15:
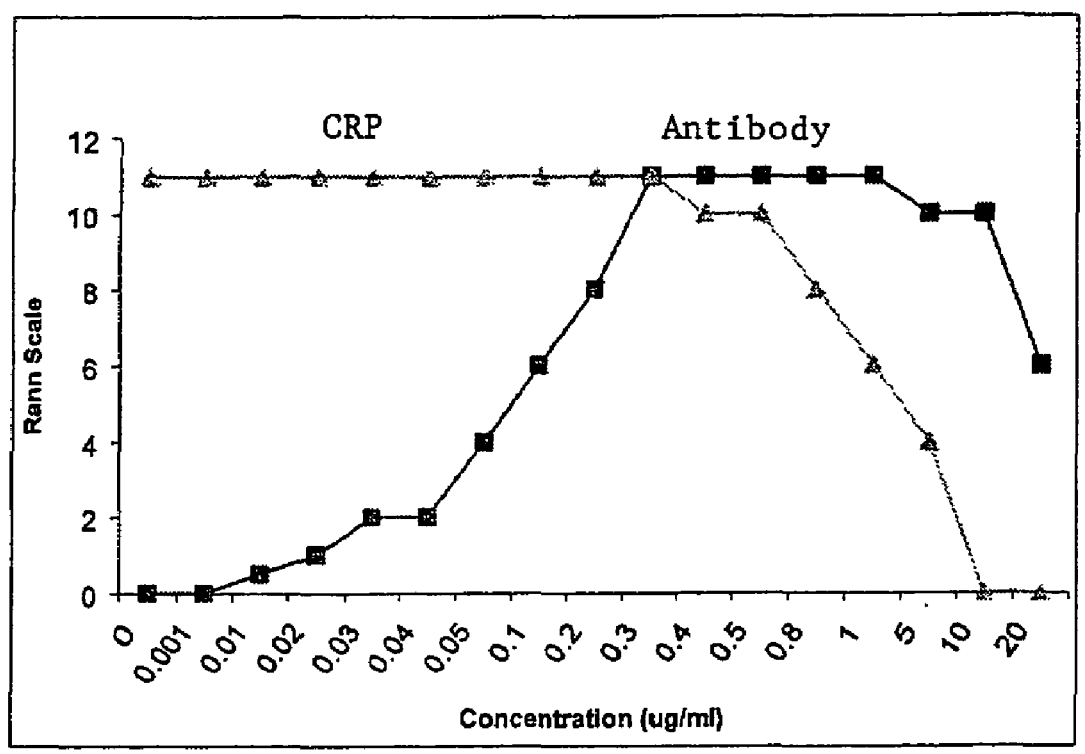
FIG. 15 is the dose response curve for Example 9 in which the Rann score of the detection zone and indicator zone are plotted versus CRP concentration for a gold particle size of 40 nanometers, a conjugate optical density of 2.5, an antibody line concentration of 0.1 milligrams per milliliter, and a CRP line concentration of 0.5 milligrams per milliliter.

The results are shown in FIGS. 11-15. As shown in FIGS. 11-12, for instance, an antibody concentration of 0.5 mg/ml at the detection zone resulted in either no signal or a faint signal (i.e., Rann=1) at the indicator zone between CRP concentrations of 0.2 to 20 micrograms per milliliter. Decreasing the antibody concentration to 0.1 mg/ml (FIGS. 13-14) increased the CRP line ("indicator zone") signal intensity and yielded a shallower CRP curve. Furthermore, by increasing the gold conjugate concentration to an optical density of 2.5, both the antibody and CRP lines increased in signal intensity (FIG. 15). The CRP line also began to decline near the point at which the antibody signal reached its peak (e.g., at the "hook effect" point).

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for quantitatively or semi-quantitatively detecting an analyte within a test sample, the method comprising:
   i) contacting the test sample with a porous membrane of a lateral flow device, the porous membrane being in communication with conjugated detection probes, the conjugated detection probes being capable of generating a signal, the porous membrane defining:
      a detection zone in which is immobilized a first receptive material, the first receptive material being configured to preferentially bind to the analyte, whether complexed or uncomplexed with the conjugated detection probes;
      an indicator zone located downstream from the detection zone, wherein a second receptive material is immobilized within the indicator zone, the second receptive material being configured to preferentially bind to the uncomplexed conjugated detection probes;
   ii) measuring the intensity of a detection signal produced at the detection zone and the intensity of an indicator signal produced at the indicator zone;
   iii) comparing the measured indicator signal intensity to a reference standard, the reference standard representing an intensity or range of intensities of the indicator signal at or near a saturation concentration of the analyte;
   iv) generating a dose response curve by plotting detection signal intensity for known analyte concentrations; and
   v) converting the measured detection signal intensity to an analyte concentration or range of concentrations based on whether the measured indicator signal intensity is less than, greater than, or the same as the reference standard, wherein the concentration of the analyte in the test sample is determined using a first region of the dose response curve when the measured indicator signal intensity is greater than the reference standard, or the concentration of the analyte in the test sample is determined using a second region of the dose response curve when the measured indicator signal intensity is less than the reference standard, or wherein a third region of the dose response curve is used when the measured indicator signal intensity is the same as the reference standard, the third region providing a range within which the concentration of the analyte falls.

2. The method of claim 1, wherein a calibration signal intensity is also used to generate the dose response curve.

3. The method of claim 1, wherein the detection signal intensity of the dose response curve bears an approximate linear relationship to analyte concentration within the first region.

4. The method of claim 1, wherein the detection signal intensity of the dose response curve bears an approximate linear relationship to analyte concentration within the second region.

5. The method of claim 1, wherein the indicator signal intensity bears an approximate linear relationship to analyte concentration within the third region.

6. The method of claim 1, further comprising selectively controlling the concentration of a receptive material used to generate the dose response curve to help achieve a certain sensitivity range for the dose response curve.

7. The method of claim 1, further comprising selectively controlling the concentration of conjugated detection probes used to generate the dose response curve to help achieve a certain sensitivity range for the dose response curve.

8. The method of claim 1, wherein a second test sample is diluted for contact with the porous membrane when the measured indicator signal intensity is approximately the same as the reference standard.

9. The method of claim 1, wherein the first and second receptive materials are selected from the group consisting of antibodies, antigens, haptens, protein A, protein G, protein A/G, neutravidin, avidin, streptavidin, captavidin, as well as analogs thereof.

10. The method of claim 1, wherein the second receptive material has at least one epitope in common with the analyte.

11. The method of claim 10, wherein the second receptive material includes an antigen or an analog thereof.

12. The method of claim 11, wherein the first receptive material includes an antibody or an analog thereof.

13. The method of claim 1, wherein the detection probes comprise a substance selected from the group consisting of chromogens, catalysts, luminescent compounds, radioactive compounds, visual labels, liposomes, and combinations thereof.

14. The method of claim 1, wherein the detection probes comprise a luminescent compound.

15. The method of claim 1, wherein the detection probes comprise a visual label.

16. The method of claim 1, wherein the detection probes are conjugated with a specific binding member selected from the group consisting of antibodies, antigens, haptens, protein A, protein G, protein A/G, neutravidin, avidin, streptavidin, captavidin, and analogs thereof.

17. The method of claim 1, wherein the analyte is C-reactive protein.

18. The method of claim 1, wherein the porous membrane further defines a calibration zone that is capable of producing a calibration signal.

19. The method of claim 1, wherein the porous membrane further defines a control zone.

20. A method for quantitatively or semi-quantitatively detecting an antigen within a test sample, the method comprising:
   i) contacting the test sample with a porous membrane of a lateral flow device, the porous membrane being in communication with conjugated detection probes, the conjugated detection probes being capable of generating a signal, wherein the antigen is capable of forming complexes with the conjugated detection probes, the porous membrane defining:
      a detection zone in which is immobilized a first receptive material, the first receptive material comprising an antibody or an analog thereof that is configured to preferentially bind to the antigen, whether complexed or uncomplexed with the conjugated detection probes;
      an indicator zone located downstream from the detection zone, wherein a second receptive material is immobilized within the indicator zone, the second receptive material comprising an antigen or an analog thereof that is configured to preferentially bind to uncomplexed conjugated detection probes;
   ii) measuring the intensity of a detection signal produced at the detection zone and the intensity of an indicator signal produced at the indicator zone;
   iii) comparing the measured indicator signal intensity to a reference standard, the reference standard representing an intensity or range of intensities of the indicator signal at or near a saturation concentration of the antigen;
   iv) generating a dose response curve by plotting detection signal intensity for known antigen concentrations; and
   v) converting the measured detection signal intensity to an antigen concentration or range of concentrations based on whether the measured indicator signal intensity is less than, greater than, or the same as the reference standard, wherein the concentration of the antigen in the test sample is determined using a first region of the dose response curve when the measured indicator signal intensity is greater than the reference standard, or the concentration of the antigen in the test sample is determined using a second region of the dose response curve when the measured indicator signal intensity is less than the reference standard, or wherein a third region of the dose response curve is used when the measured indicator signal intensity is the same as the reference standard, the third region providing a range within which the concentration of the antigen falls.

21. The method of claim 20, wherein a calibration signal intensity is also used to generate the dose response curve.

22. The method of claim 20, wherein the detection probes comprise a luminescent compound or a visual label.

23. The method of claim 20, wherein the antigen is C-reactive protein.

* * * * *